(12) United States Patent
Turpening et al.

(10) Patent No.: US 6,347,551 B1
(45) Date of Patent: Feb. 19, 2002

(54) ACOUSTIC TREE AND WOODEN MEMBER IMAGING APPARATUS

(75) Inventors: Roger M. Turpening, Andover; Zhenya Zhu, Quincy; Joseph R. Matarese, Cambridge, all of MA (US); Carol E. Lewis, Fairbanks, AK (US)

(73) Assignees: University of Alaska, Fairbanks, AK (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/622,728
(22) PCT Filed: Feb. 25, 1999
(86) PCT No.: PCT/US99/04092
§ 371 Date: Nov. 6, 2000
§ 102(e) Date: Nov. 6, 2000
(87) PCT Pub. No.: WO99/44050
PCT Pub. Date: Sep. 2, 1999

Related U.S. Application Data
(60) Provisional application No. 60/076,139, filed on Feb. 27, 1998.

(51) Int. Cl.⁷ ................................................ G01N 29/04
(52) U.S. Cl. ........................ 73/628; 73/597; 73/598; 73/599; 73/600
(58) Field of Search ......................... 73/597, 598, 599, 73/600, 602, 634, 641, 628

(56) References Cited

U.S. PATENT DOCUMENTS

| | | |
|---|---|---|
| 369,230 A | 8/1887 | Chappel |
| 395,949 A | 1/1889 | Cade |
| 750,973 A | 2/1904 | Hinkley |

(List continued on next page.)

OTHER PUBLICATIONS

Ross, Robert J., DeGroot, Rodney C. and Nelson, William J., "Nondestructive Evaluation of Biologically Degraded Wood," Nondestructive Characterization of Materials VI, 1994, pp. 545–550, Plenum Press, New York.

Schad, Kristin C., Schmoldt, Daniel L. and Ross, Robert J., "Nondestructive Methods for Detecting Defects in Softwood Logs," Research Paper FPL–RP–546, 1996, pp. 1–13, U. S. Dept. of Agriculture, Forest Service, Forest Products Laboratory, Madison, WI.

Fuller, James J., Ross, Robert J. and Dramm, John R., "Honeycomb and Surface Check Detection Using Ultrasonic Nondestructive Evaluation," Research Note FPL–RN–0261, 1994, pp. 1–6, U. S. Dept. of Agriculture, Forest Service, Forest Products Laboratory, Madison, WI.

Ross, Robert J., Geske, Earl A., Larson, Gary R. and Murphy, Joseph F., "Transverse Vibration Nondestructive Testing Using a Personal Computer," Research Paper FPL–RP–502, 1991, pp. 17, U. S. Dept. of Agriculture, Forest Service, Forest Products Laboratory, Madison, WI.

(List continued on next page.)

Primary Examiner—Hezron Williams
Assistant Examiner—Jacques Saint-Surin
(74) Attorney, Agent, or Firm—Steven J. Weissburg

(57) ABSTRACT

An ultrasonic computed tomography tree or log scanner has a plurality of ultrasonic transceivers carried on a belt (102) sized to encircle a tree (100). The belt includes an apparatus for engaging is tightly around the tree (104). The transceivers are strapped around the tree, and their mutual relative distances are known. Electronic circuitry energizes the transmitters in a known sequence. The signals received at each of the receivers are also collected and analyzed. Computed tomographic techniques analyze the time of arrival of the acoustic pulse that is first to arrive at each receiver. A signal processor generates a two-dimensional image of a slice of the tree (110) at the locus of the belt.

31 Claims, 31 Drawing Sheets

U.S. PATENT DOCUMENTS

| | | | |
|---|---|---|---|
| 2,832,630 A | | 4/1958 | Sterling |
| 2,908,161 A | | 10/1959 | Bincer |
| 3,066,525 A | | 12/1962 | Harris |
| 3,248,933 A | | 5/1966 | Stebbins |
| 3,279,242 A | | 10/1966 | Megoloff |
| 3,426,585 A | | 2/1969 | Zemanek, Jr. et al. |
| 3,877,294 A | * | 4/1975 | Shaw .......................... 73/67.2 |
| 4,019,373 A | | 4/1977 | Freeman et al. |
| 4,108,004 A | | 8/1978 | Murakami |
| 4,270,389 A | | 6/1981 | Shiraiwa et al. |
| 4,562,540 A | * | 12/1985 | Devaney ...................... 73/602 |
| 4,926,691 A | * | 5/1990 | Franklin et al. ............... 73/579 |
| 5,097,881 A | | 3/1992 | Mack |
| 5,307,679 A | | 5/1994 | Ross |
| 5,396,799 A | | 5/1995 | Ross |
| 5,760,308 A | * | 6/1998 | Beall et al. .................... 73/644 |
| 5,804,728 A | * | 9/1998 | Beall et al. .................... 73/598 |
| 6,092,418 A | * | 7/2000 | Schafer et al. ................ 73/598 |

OTHER PUBLICATIONS

Ross, Robert J. and Pellerin, Roy F., "Nondestructive testing for Assesing Wood Members in Structures: A Review," General Technical Report FPL–GTR–70, 1994, pp. 1–40, U. S. Dept. of Agriculture, Forest Service, Forest Products Laboratory, Madison, WI.

Ross, Robert J., Ward, James C. and Tenwolde, Anton, "Indentifying Bacterially Infected Oak by Stress Wave Nondestructive Evaluation," Research Paper FPL–RP–512, 1992, pp. 1–6, U. S. Dept. of Agriculture, Forest Service, Forest Products Laboratory, Madison, WI.

Verkasalo, Erkki, Ross, Robert J., Tenwolde, Anton and Youngs, Robert L., "Properties Related to Drying Defects in Red Oak Wetwood," Research Paper FPL–RP–516, 1993, pp. 1–10, U. S. Dept. of Agriculture, Forest Service, Forest Products Laboratory, Madison, WI.

Ross, Robert J, Ward, James C. and Tenwolde, Anton, "Stress wave nondestructive evaluation of wetwood," Forest Products Journal, July/August 1994, pp. 79–83, vol. 44, No. 7/8.

Ross, Robert J., Fuller, James J. and Dramm, John R., "Nondestructive Evaluation of Wetwood and Honeycomb," Hardwood Symposium Proceedings, May 17–20, 1995, pp. 61–67.

Ross, Robert J. and Pellerin, Roy F., "Nondestructive testing for in–place assessment of wood members, " Wood products for engineered structures: issues affecting growth and acceptance of engineered wood products (Bender, Donald A. (editor)), Proceedings 47329, Nov. 11–13, 1992, Las Vegas Madison, WI: Forest Products Society; 1993, pp. 176–179, (p. 177 is missing).

Ross, Robert J., Degroot, Rodney C., Nelson, William J. and Lebow, Patricia K., "The Relationship Between Stress Wave Transmission Characteristics and the Compressive Strength of Biologically Degraded Wood," Forest Products Journal, May 1997, pp. 89–93, vol. 47 No. 5.

Ross, Robert J., McDonald, Kent A., Green, David W. and Schad, Kristin C., "Relationship Between Log and Lumber Modulus of Elasticity," Forest Products Journal, February 1997, pp. 89–92, vol. 47, No. 2.

Pellerin, Roy F., DeGroot, Rodney C. and Esenther, Glenn R., "Nondestructive Stress Wave Measurements of Decay and Termite Attack in Experimental Wood Units," pp. 319–352, Note: publication source and date uncertain.

Ross, Robert J. and DeGroot, Rodney C., Manuscript transmittal for project entitled "Scanning Technique to Identify Biologically Degraded Wood, " U.S. Dept. of Agriculture, Forest Products Laboratory, prepared for publication in Experimental Techniques, written April 1996, revised September 1997, no publication date. Not Admitted To Be Prior Art.

Matarese, Joseph R., "Nonlinear Traveltime Tomography," a thesis submitted to the Department of Earth, Atmospheric, and Planetary Sciences at Massachusetts Institute of Technology, in partial fulfillment of the requirements for the degree of Doctor of Philosophy in Geophysics, in 1993.

* cited by examiner

ACOUSTIC TREE AND WOODEN MEMBER IMAGING APPARATUS

This application is based on and claims priority to U.S. Prov. App. No. 60/076,139, filed on Feb. 27, 1998.

BACKGROUND

This invention relates to the non-destructive analysis of standing and felled trees and poles, such as utility poles, and more particularly to generating two and three dimensional images of such trees that indicate their internal structure.

Trees and utility poles, such as telephone poles, are subject to various kinds of interior deteriorating and rotting conditions that are not evident from indicia outside of the tree or pole. Trees can undergo such internal rot for years, without noticeable symptoms to the leaves, bark or other observable structures. However, once the tree is cut down, and sawn up for use as lumber, paper, veneer, etc., the presence of large areas of rot greatly diminish the useability of the tree. In addition to rot, the presence of other internal structures, such as voids and knots, affects the uses to which a particular tree or tree section can be put. Thus there are many reasons to know the internal structure or condition of both standing and recently felled trees.

Owners and prospective purchasers of tracts of trees desire to know the general condition of the trees before they are purchased, or before efforts are made to log any significant percentage of such trees. Similarly, prospective purchasers of individual trees would like to be able to assess their condition before purchase. Arborists, or those responsible for the health of forests and trees would like to be able to assess the spread of any transmissible disorder of such trees, in order to better stem the movement of any such condition through a forest. Arborists are also interested in the type of rotting condition experienced by the tree, which may indicate the cause and treatment. Different types of rot are evidenced by different patterns of decay. Environmentalists who are interested in maintaining dead trees standing, such as for habitation by spotted owls and other animals, will be able to identify trees that are not worth logging, which may then be saved from logging because the lumber company would have no interest in felling a rotten tree.

Persons with militant anti-lumber attitudes have also been known to drive stainless steel spikes randomly into stands of trees. If such a spike is encountered by a saw during the felling or processing of such a tree, it can cause significant damage to equipment and injury to persons. The spikes can not be located by magnetic techniques, because stainless steel is not magnetically attractive.

At the level of an individual tree, if a lumber mill operator knows of the location inside a felled tree where there are rotting conditions, it is possible to make better use of the tree. For instance, if one were to know that the center of a tree is rotted, with the outside being in good shape, that tree could be dispatched to a veneer mill, which would "peel" the outer, high quality wood from the tree, stopping when the rotted inner section is reached. In addition to rot, it is also helpful to know the locations of other internal non-uniformities, such as knots and voids, when sorting logs, or orienting logs for various mill operations. Such triage could be performed on whole trees, or on sections of trees.

Many of the foregoing operations must be performed in the field on standing trees, far from any roads or mills. Thus, any equipment that is required to perform such operations must be small enough and light enough so that it can be carried to the standing tree by a single user. Further, it must be operable under battery or other portable power sources for a length of time that is long enough to make its use worth the effort of transporting it to the site.

Many problems similar to the foregoing also exist with standing wooden poles, such as utility poles, including telephone poles. Once in place and tied into a network, it is very expensive to remove and replace them. However, such poles do suffer from deterioration, such as rot and bug infestation, and must be replaced from time to time. Other types of wooden members that require knowledge about their internal condition include piers, pilings and scaffolds. These poles and wooden members are also often far from roads or are not readily accessible to heavy machinery.

Accordingly, for the foregoing reasons, there is a need for a relatively small, lightweight, long life apparatus that can generate a two dimensional image of the interior of a standing tree or pole or recently felled tree. There is also need for such a device that would operate quickly enough to give the operator an essentially immediate image of the tree or pole under inspection so that decisions of disposition of the tree or pole can be made in the field. There is further a need for a device that can readily be attached and removed from a tree or pole, to provide an image at different locations along a tree or pole , and further, for a device that can generate a three-dimensional representation of a standing tree or pole or recently felled tree in the field.

SUMMARY

A preferred embodiment of the apparatus according to the invention is an ultrasonic computed tomography tree, pole, or log scanner. A plurality of ultrasonic transceivers (each of which can both transmit and receive ultrasonic impulses) are carried on a belt that is sized to encircle a typical tree or pole of the size to be examined. The belt includes a cinch or chain or other mechanical apparatus for engaging it very tightly around the circumference of the tree or pole to be examined. The transceivers are spaced around the tree or pole, and their mutual relative distances are known. Electronic circuitry is provided for energizing the transmitters in a known sequence. The signals that are received at each of the receivers are also collected and analyzed. Using computed tomographic techniques to analyze the time of arrival of the acoustic pulse that is first to arrive at each receiver, a signal processor generates a two dimensional image of a slice surface of the tree or pole at the locus of the belt. In addition to the time of arrival of the first wave to arrive, the attenuation of the energy of the first arriving wave also provides additional information that can be used in conjunction with the images that are based on the arrival time. The signal processing and transceiver controlling are performed by portable, lap-top type computers or smaller computing devices, such as PDAs, such as the Palm Pilot™, sold by 3Com.

The transceivers may include spike-like engaging portions, that are pressed strongly into the bark of the tree to ensure good acoustic coupling. A radar apparatus is also optionally provided to help to determine the diameter of trees whose cross-sections diverge greatly from circular. The transceivers may be coupled to the signal processor over an infra-red channel. The battery power supply for the apparatus may be carried by the belt, or it may be separate.

According to another preferred embodiment of the invention, at least two, and preferably three belts, each belt carrying a plurality of transceivers, as discussed above, are spaced longitudinally along the section of tree or pole, for instance one to three feet apart from each other. In such an arrangement, again, pulses from individual transmitters are received at each of the receivers, and, based on computed tomographic analysis, the internal condition of the volumetric portion of the tree is determined over all three spatial dimensions.

Another preferred embodiment of the method of the invention is a method for the non-destructive examination of trees, poles, and logs, which includes the steps of acoustically coupling a plurality of ultrasonic transceivers to a tree or pole. The transmitters are pulsed according to a known order, and the signals from each transmitter are received at each of the receivers. The time of reception and the attenuation from the original signal is noted for each receiver. Using the time of arrival information, a two dimensional image is generated, by applying computed tomographic procedures to the data. The two dimensional image is displayed on a human perceptible device. In addition to the time of arrival data, the attenuation data may also be used to create an independent image or enhance the image of the internal structure of the tree, pole, or log. A similar method is conducted for the three dimensional data embodiment of the invention discussed above.

BRIEF DESCRIPTION OF THE DRAWINGS

These and other features, aspects, and advantages of the present invention will become better understood with regard to the following description, appended claims and accompanying drawings, where:

FIGS. 6A–6L show graphically for each transceiver, the signal that is received at all eleven other transceivers, when the transceiver in question acts as the source, sending a pulse through a rotten log from a tree;

DETAILED DESCRIPTION

Figure 1:
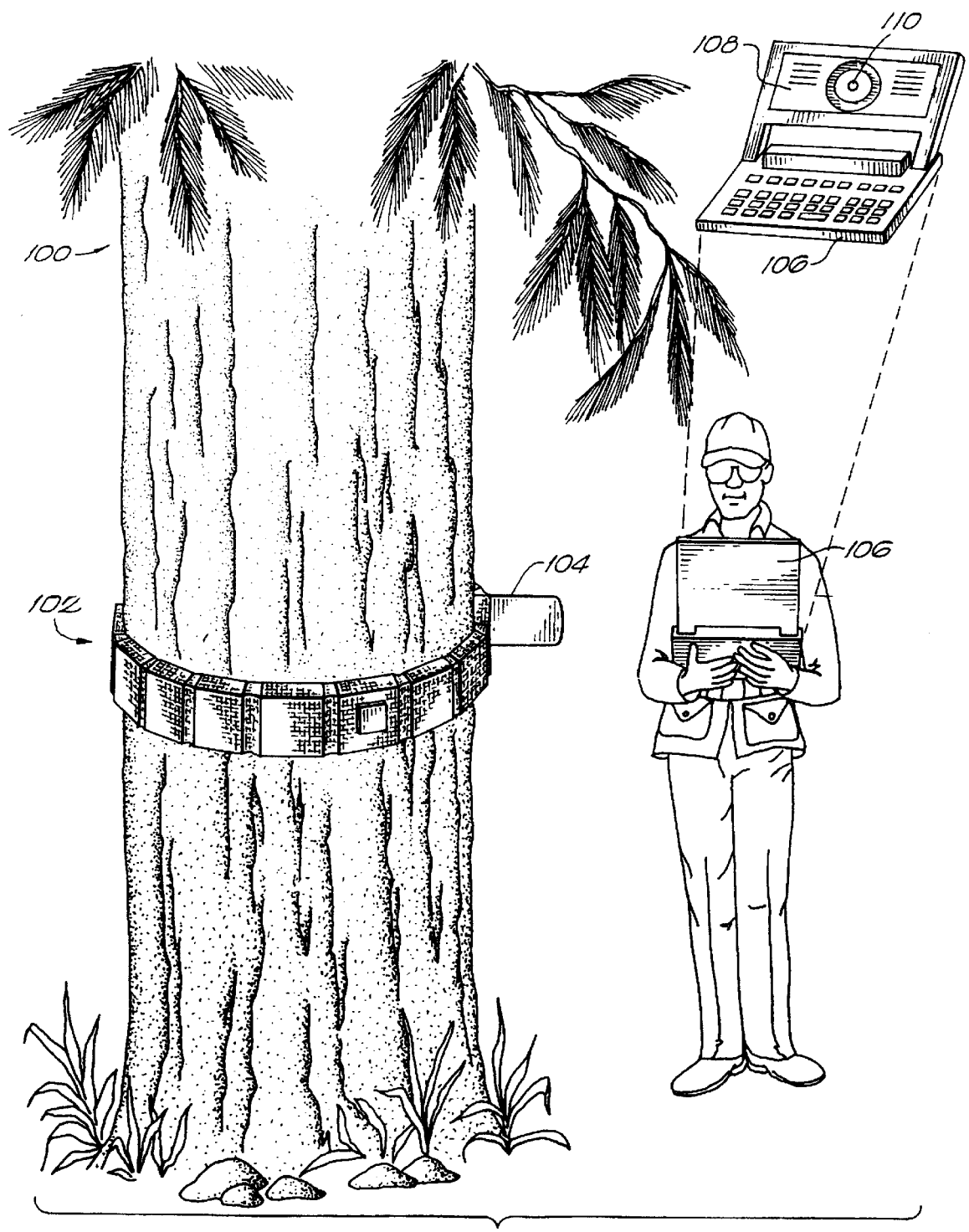
FIG. 1 is a schematic view of an embodiment of an apparatus of the invention, with a transceiver belt engaged around a tree, and a user holding a computer terminal that houses signal processing components of the invention.

A preferred embodiment of the present invention is shown schematically with reference to FIG. 1. A transducer belt 102 is secured around a standing tree 100. The belt is secured by a clamping device 104, partly obscured by the tree. A portable, hand held control unit 106 is shown schematically being held by a user, both from the front and the back. On a display screen 108, the control unit displays a two dimensional image 110 of a cross-sectional slice surface of the tree 100, as generated by the apparatus of the invention.

The invention can also be used on other wooden members, such as felled trees, logs, and even large sections of sawn logs. It can also be used on standing poles, such as utility poles including telephone poles, piers, dock supports, pilings and scaffolding. However, for simplicity, only the use with standing trees will be discussed herein, but it will be understood that the other uses just mentioned are also contemplated. In the few circumstances where it matters whether the subject of observation is a standing tree, a utility pole, or a felled tree or log, etc., that is explicitly mentioned. If not mentioned, it should be assumed that the apparatus described can be used on the other wooden members listed, in essentially the same manner.

Figure 2:
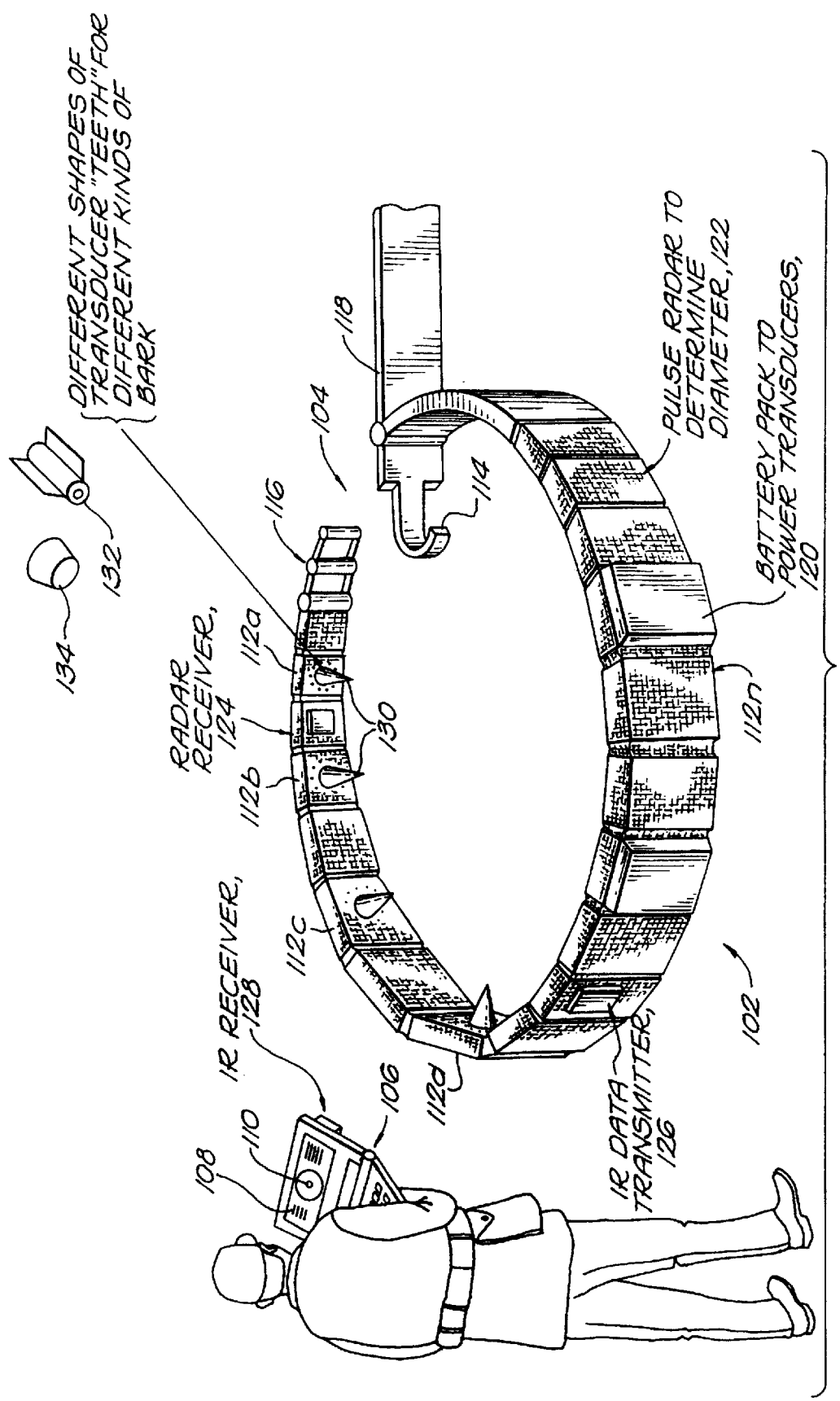
FIG. 2 is a schematic view of a transceiver belt of the invention, as shown in FIG. 1, not engaged with a tree or other wooden member.

The transducer belt 102 is shown in more detail with reference to FIG. 2, where a belt is shown apart from a tree or log to be examined. The belt includes a tightening apparatus 104, which, in this case is shown as having a hook 114 and link 116 that are tightened by a lever 118. This tightening arrangement may be similar to that used by an automobile oil filter wrench. The belt carries along its length a plurality of spaced apart ultrasonic transducers 112a, 112b, 112c, 112d, . . . 112n, which are each a combination transmitting and receiving transceiver. Also carried on the belt is a radar pulse unit 122 and receive unit 124, whose function is discussed below, and a battery pack 120 to power the transceivers and radar units.

The belt may also optionally include an infra-red (IR) band data transmitter 126, which communicates to the control unit through an IR receiver 128. The IR transmitter and receiver are each transmitting and receiving transceivers, for two way communication between the transducer belt and the control unit.

Each of the transceivers includes a spike-like tooth 130, to help couple the ultrasonic energy from the transceiver into and out of the tree. Depending on the type of bark and transducer, other shapes, such as shown at teeth 132 and 134 may be used. In some cases, it is beneficial to use a coupling agent, such as petroleum jelly, to couple the energy. In such a case, the cup like tooth 134 may be more effective. Choice of the appropriate tooth may be routinely made by the designer. The ultrasonic waves of interest are compressional waves that are transmitted through the body of the tree.

Figure 3:
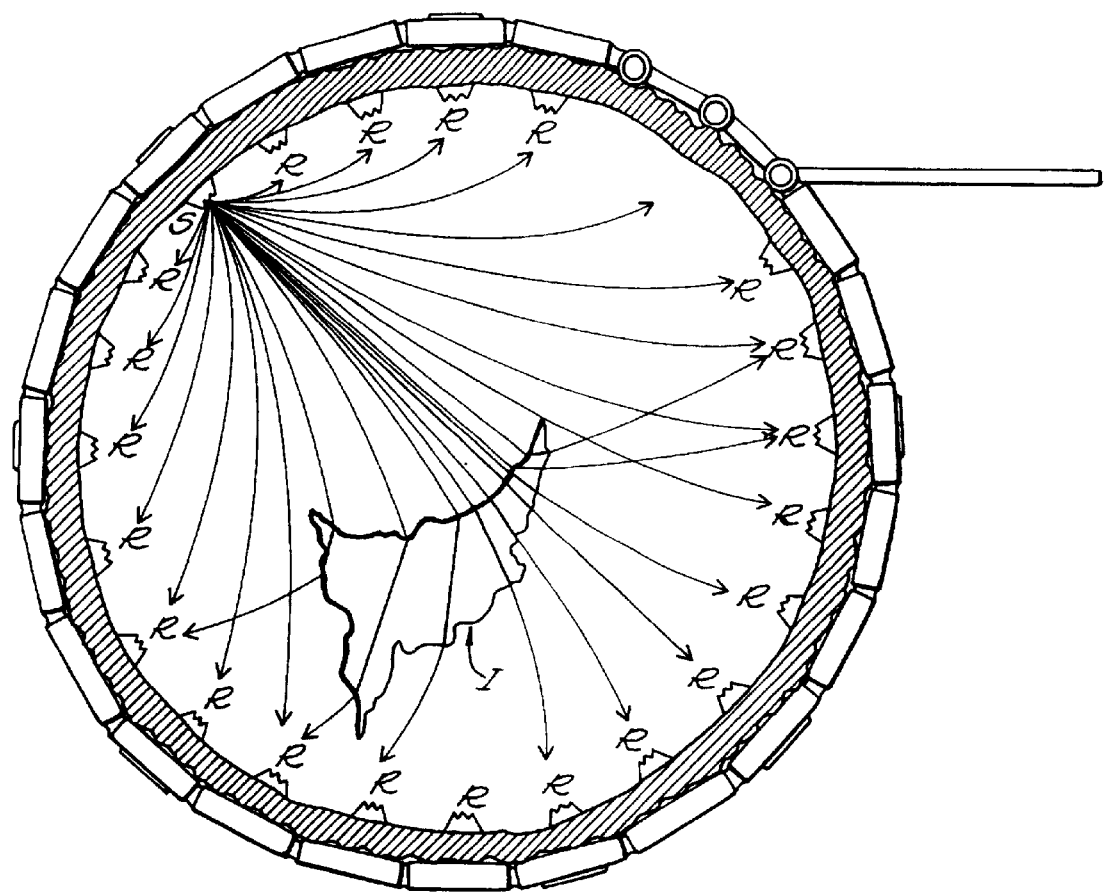
FIG. 3 shows schematically, in cross section, a plurality of transceivers, one acting as a source transmitter, the others as receivers, positioned around a tree, along with indications of the paths along which ultrasound pulses may travel.

A typical arrangement of the transceivers is shown with reference to FIG. 3, which is a schematic cross-sectional view of a belt, engaged with a tree. A plurality of twenty-two transceivers, (R) are arranged around a tree. At the moment shown, the transceiver identified as S is acting as the source of ultrasonic energy, and the others, identified as R, are all acting as receivers. At the next moment, the transceiver located clockwise one step from the S transceiver may become the source. The paths of acoustic pulses are indicated by the arrows. These paths do not follow straight lines, particularly near the irregularity I.

The mode of operation of the apparatus of the invention is understood with reference to FIGS. 5A–5L. Each figure shows eleven traces. Each trace represents the signal received at one of the eleven transceivers, which do not include the transceiver that acted as the transmitter. The signal has been launched from a single transceiver, acting as a transmitter.

Figure 5A:
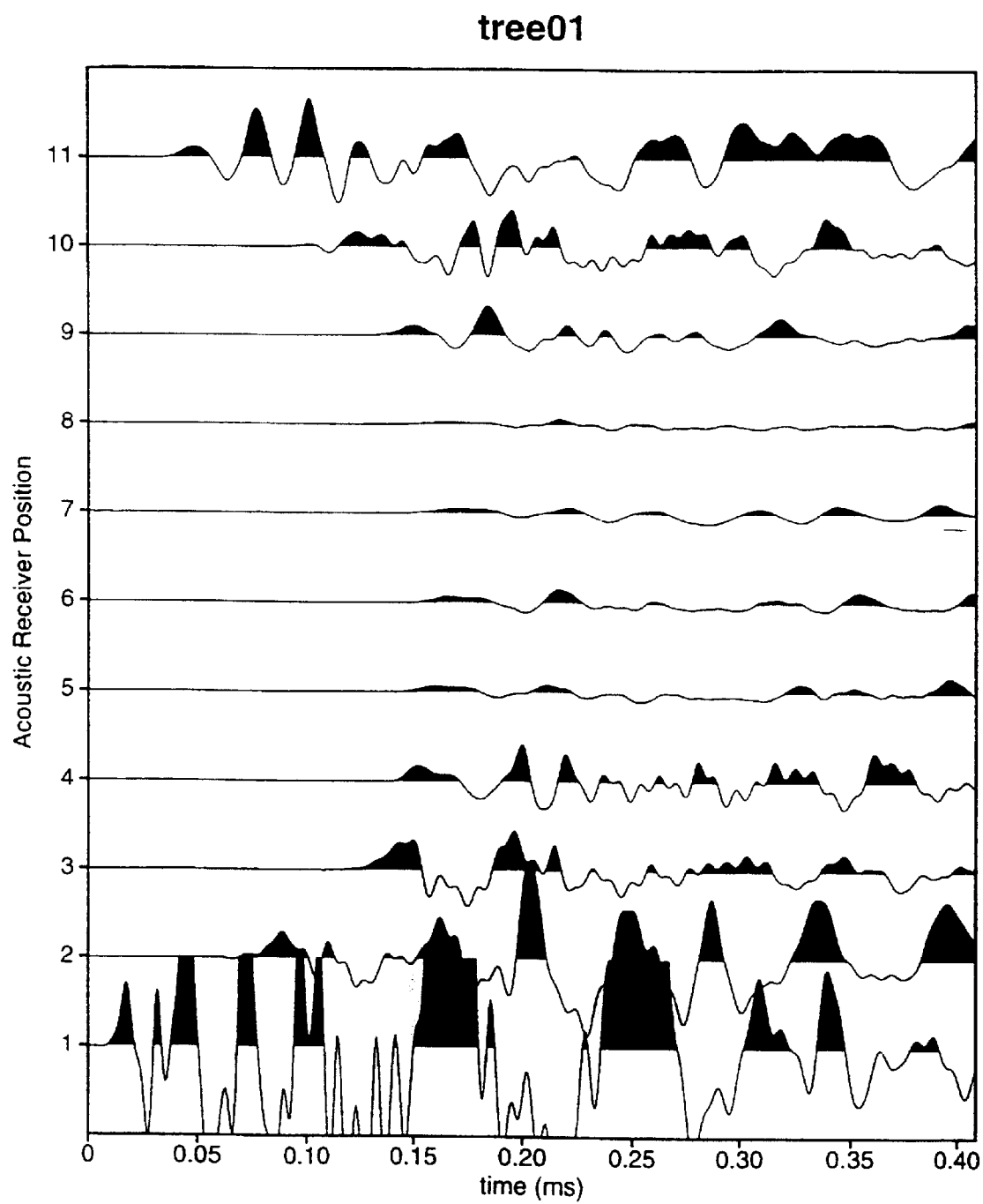
FIGS. 5A–5L show graphically for each transceiver, the signal that is received at all eleven other transceivers, when the transceiver in question acts as the source, sending a pulse through a healthy log from a tree.
Figure 5B:
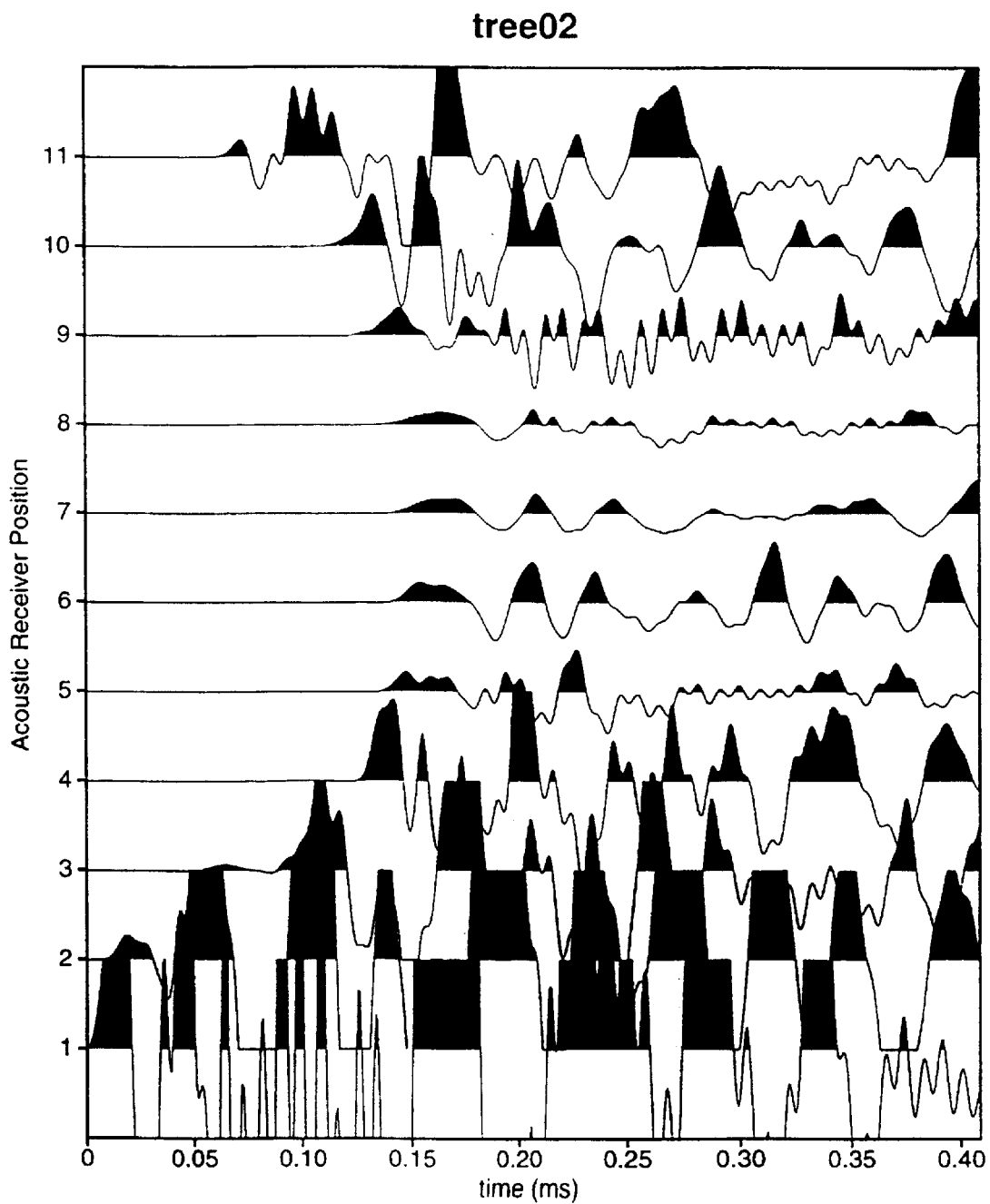

For instance, FIG. 5A shows the situation with respect to a signal that was launched from a transmitter that was positioned between those transceivers whose reception is shown on the traces numbered 1 and 11, which indicate relatively early arrival of the pulse. The transceiver at location number 6 appears to experience arrival of the first pulse after most, if not all of the other transceivers.

Figure 5C:
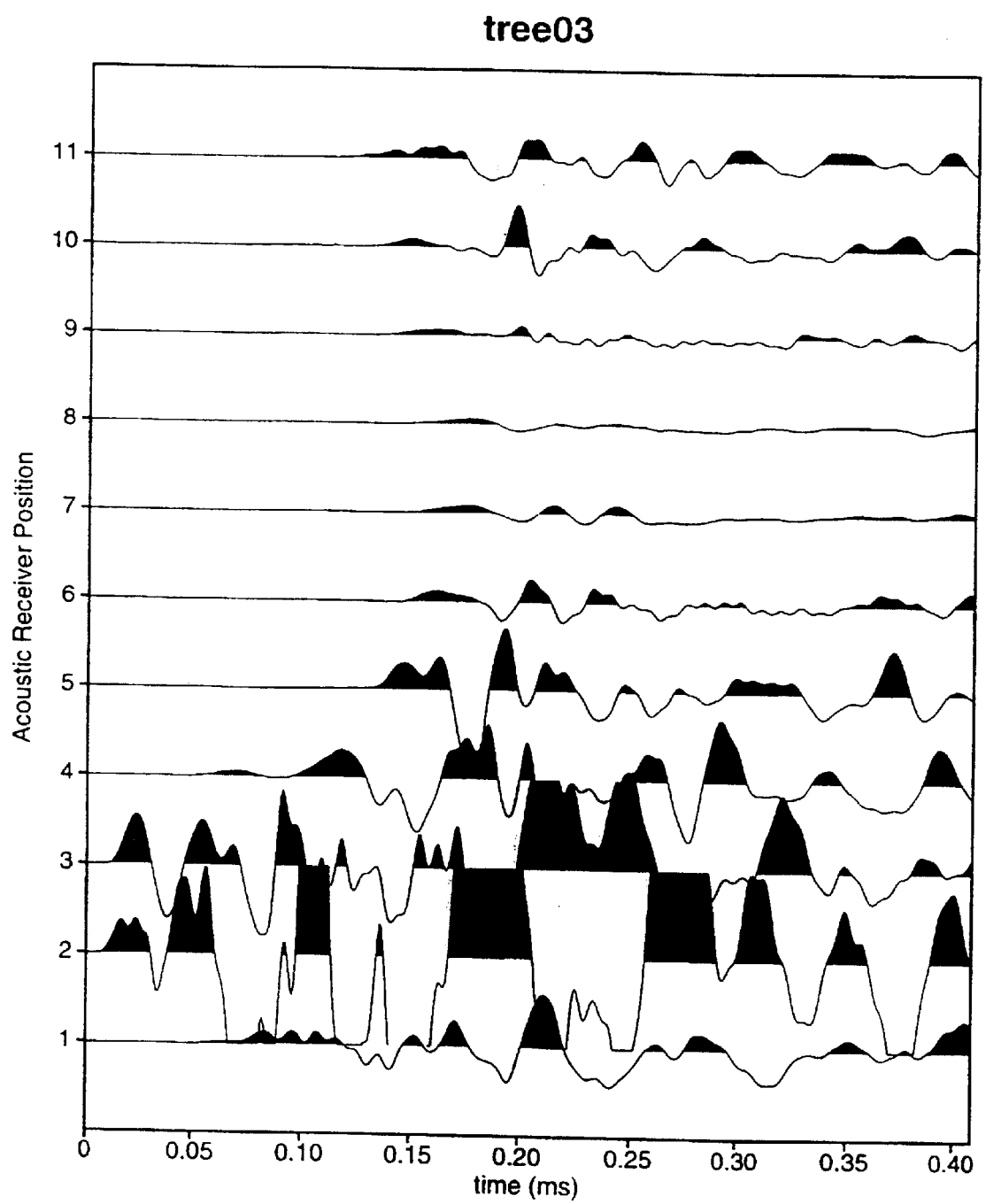
Figure 5D:
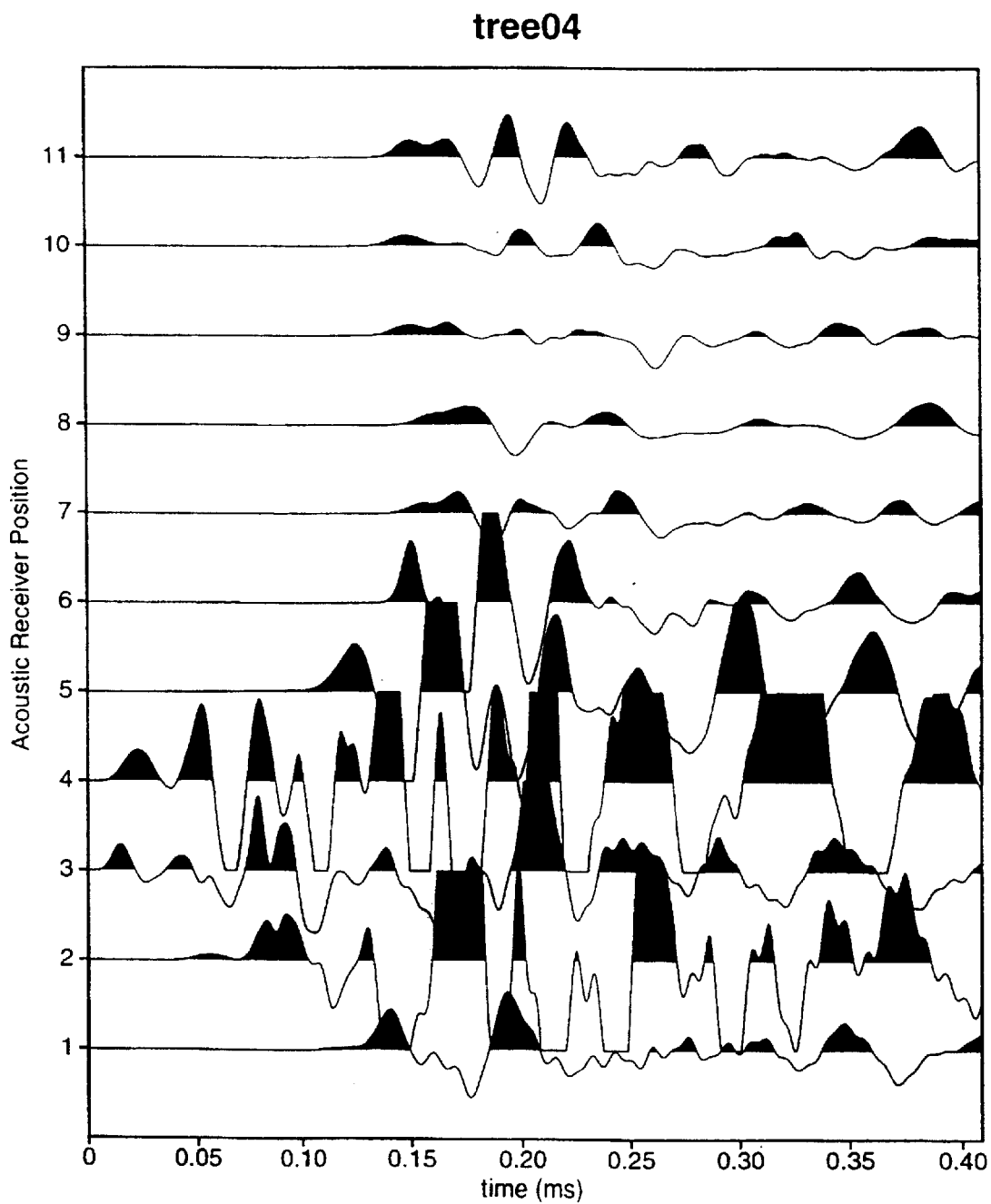
Figure 5E:
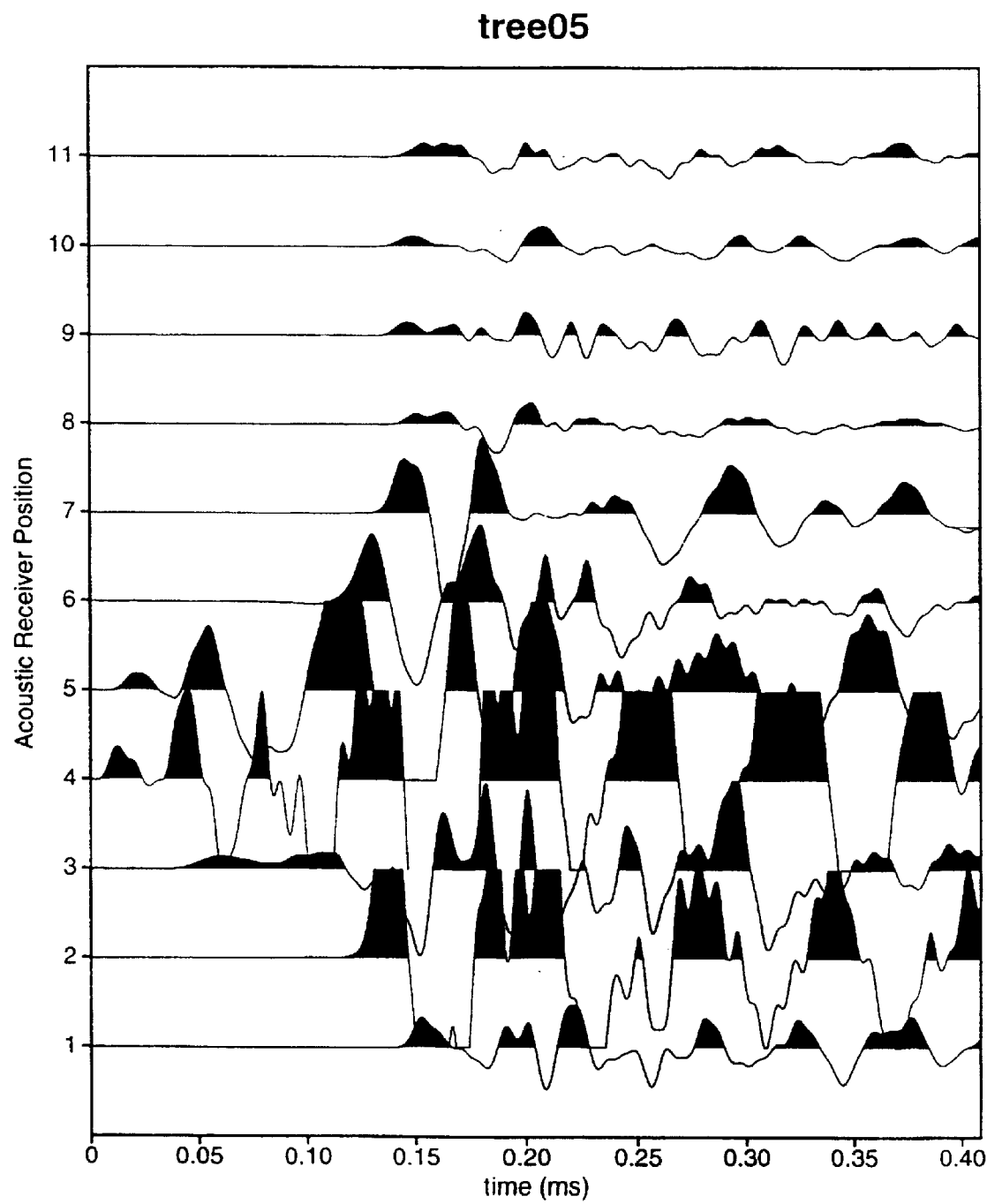
Figure 5F:
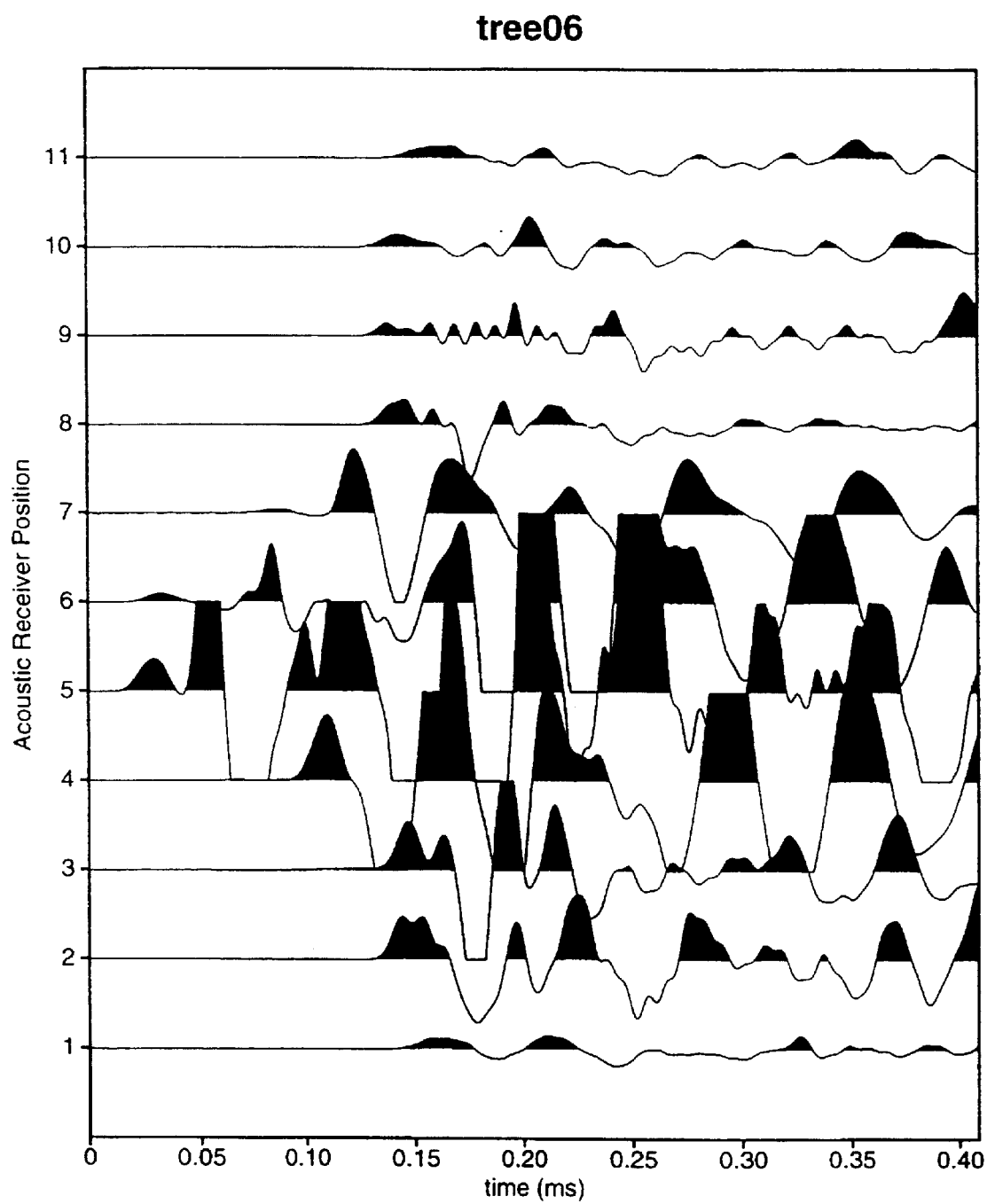
Figure 5G:
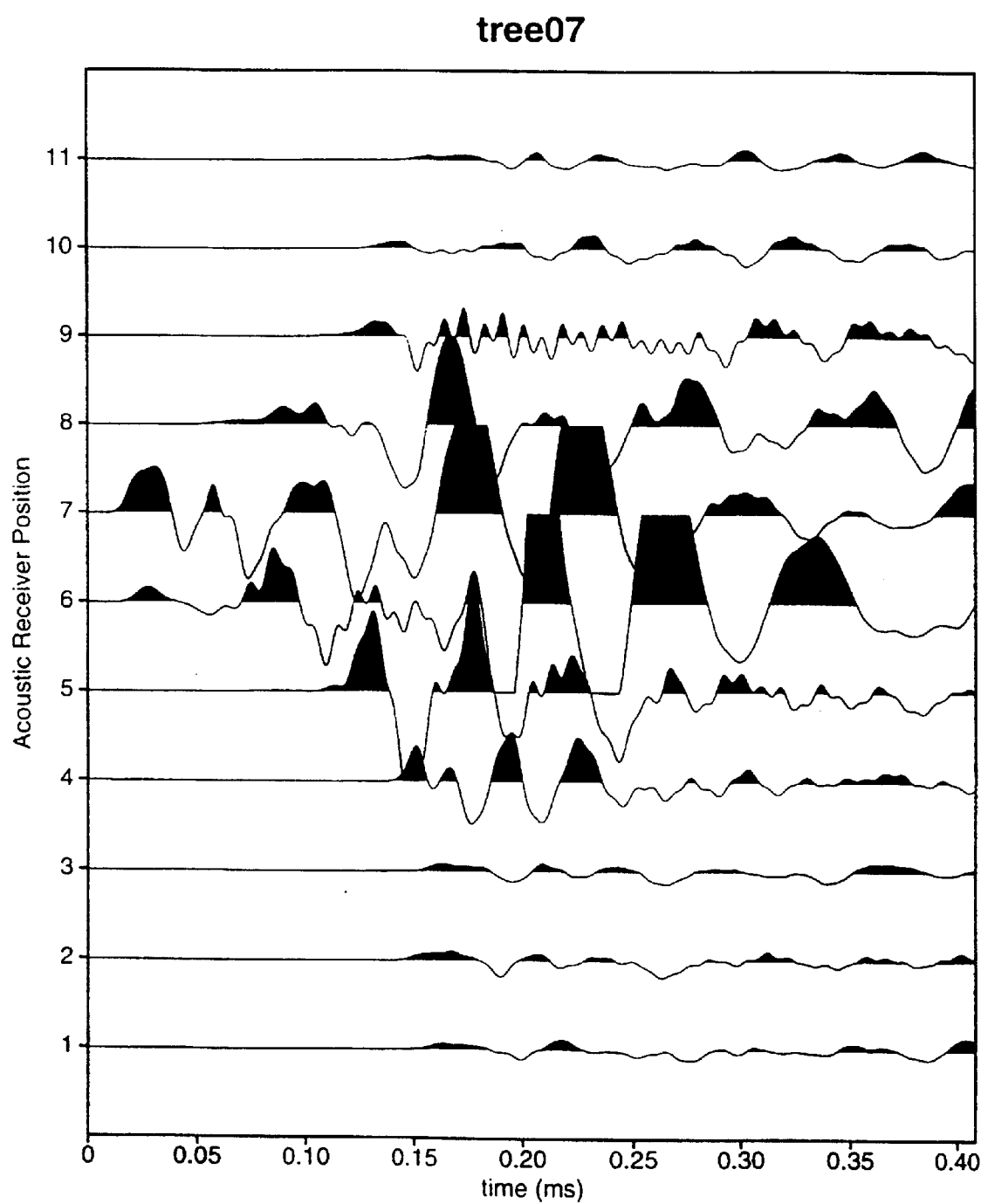
Figure 5H:
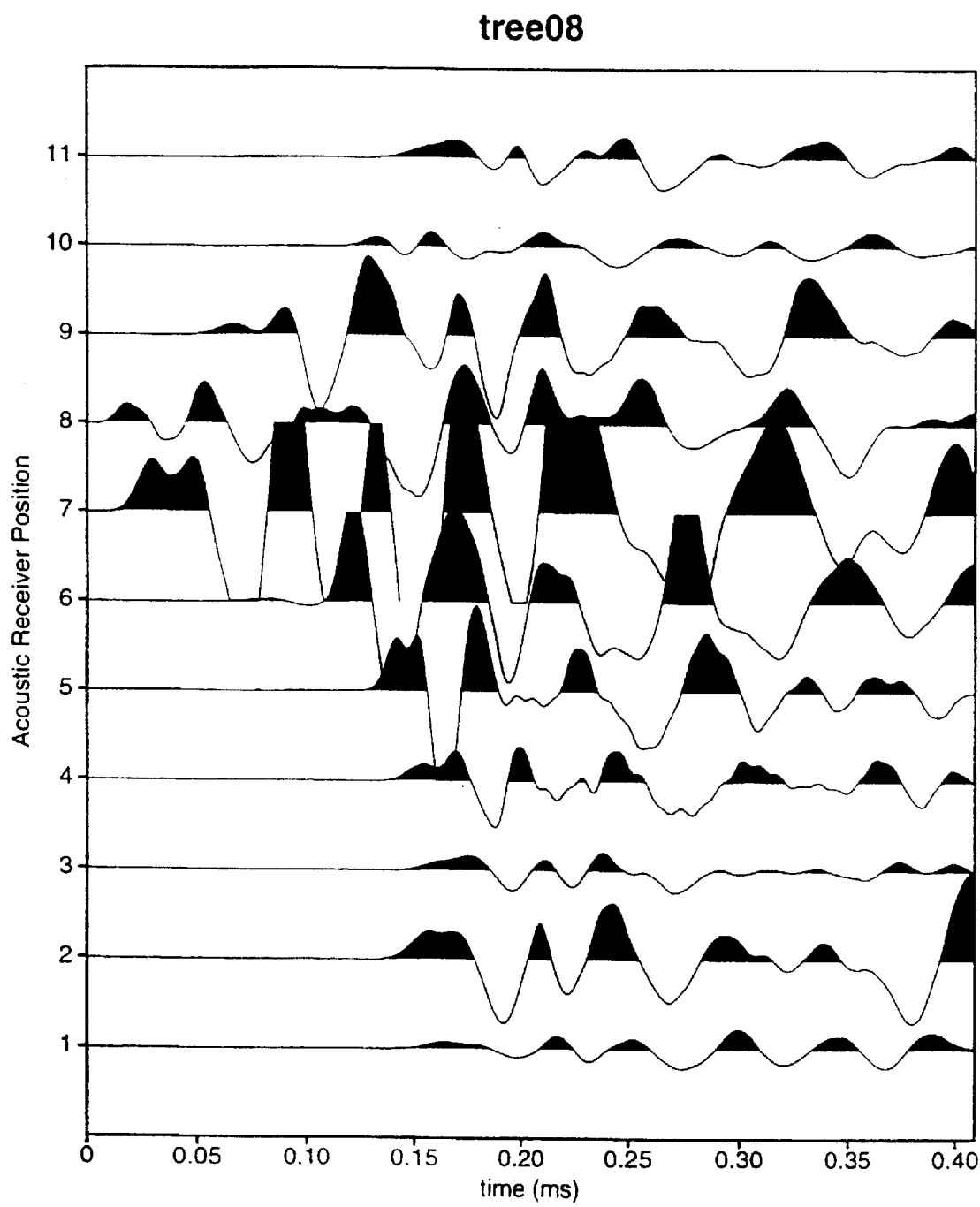
Figure 5I:
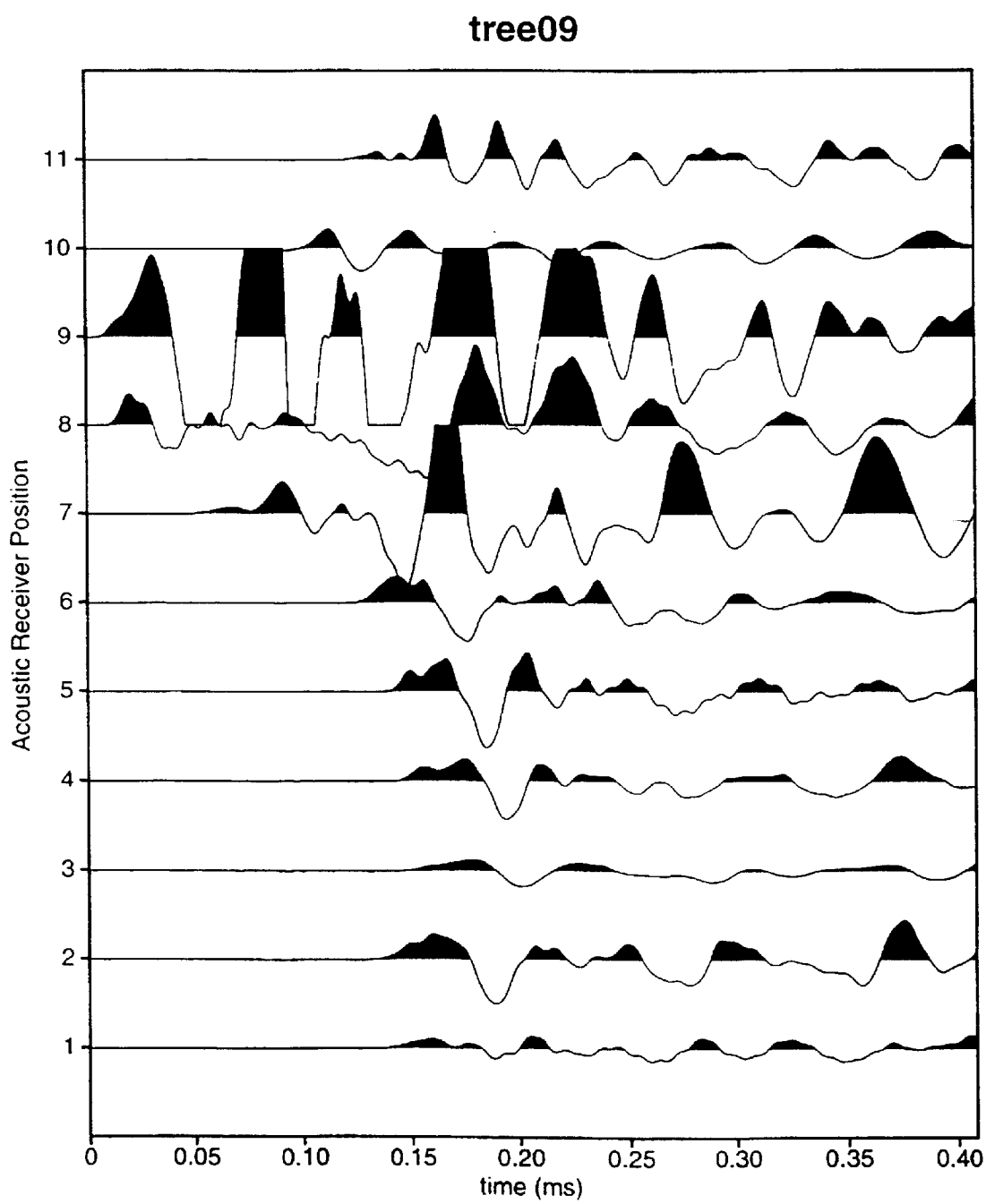
Figure 5J:
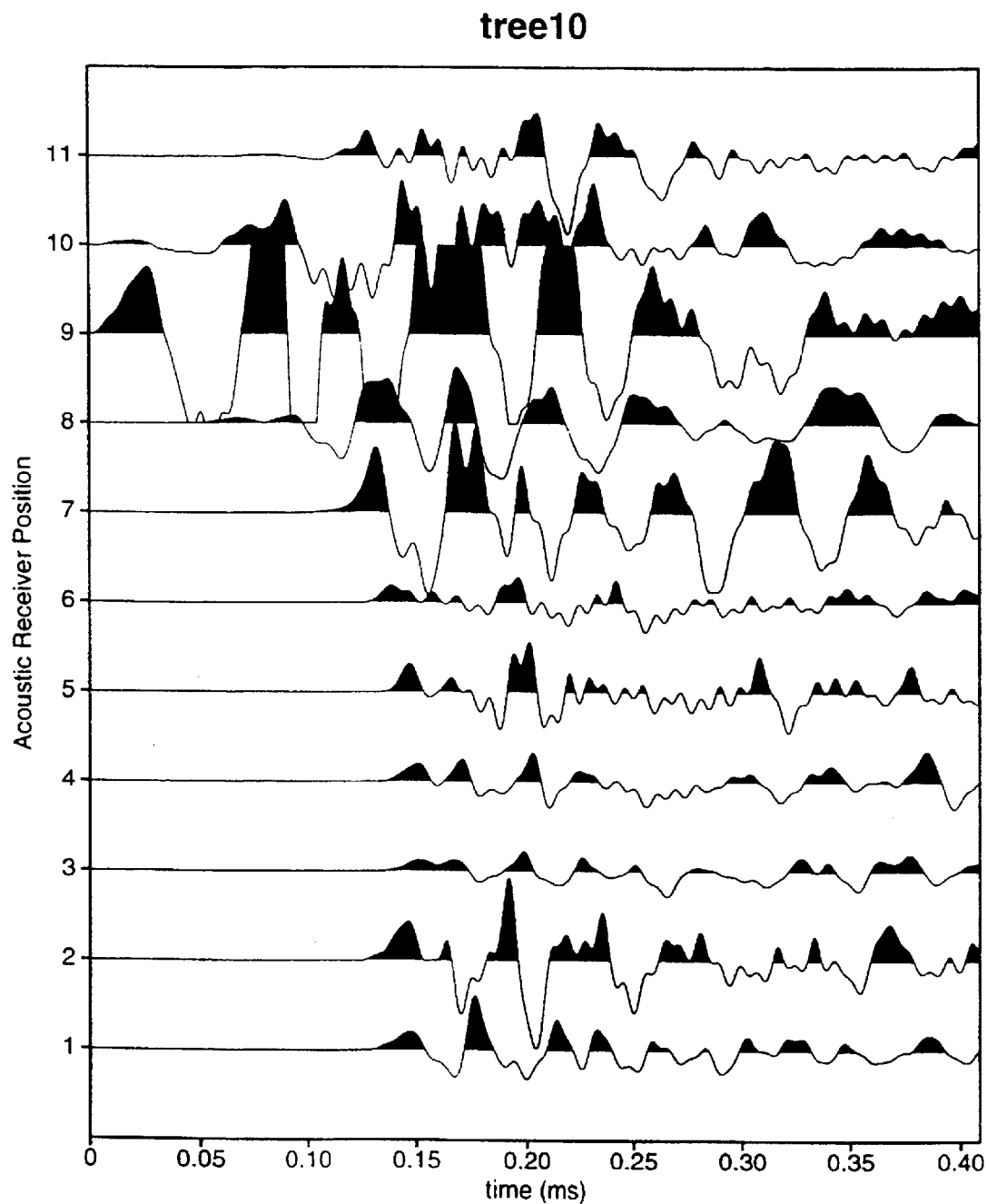
Figure 5K:
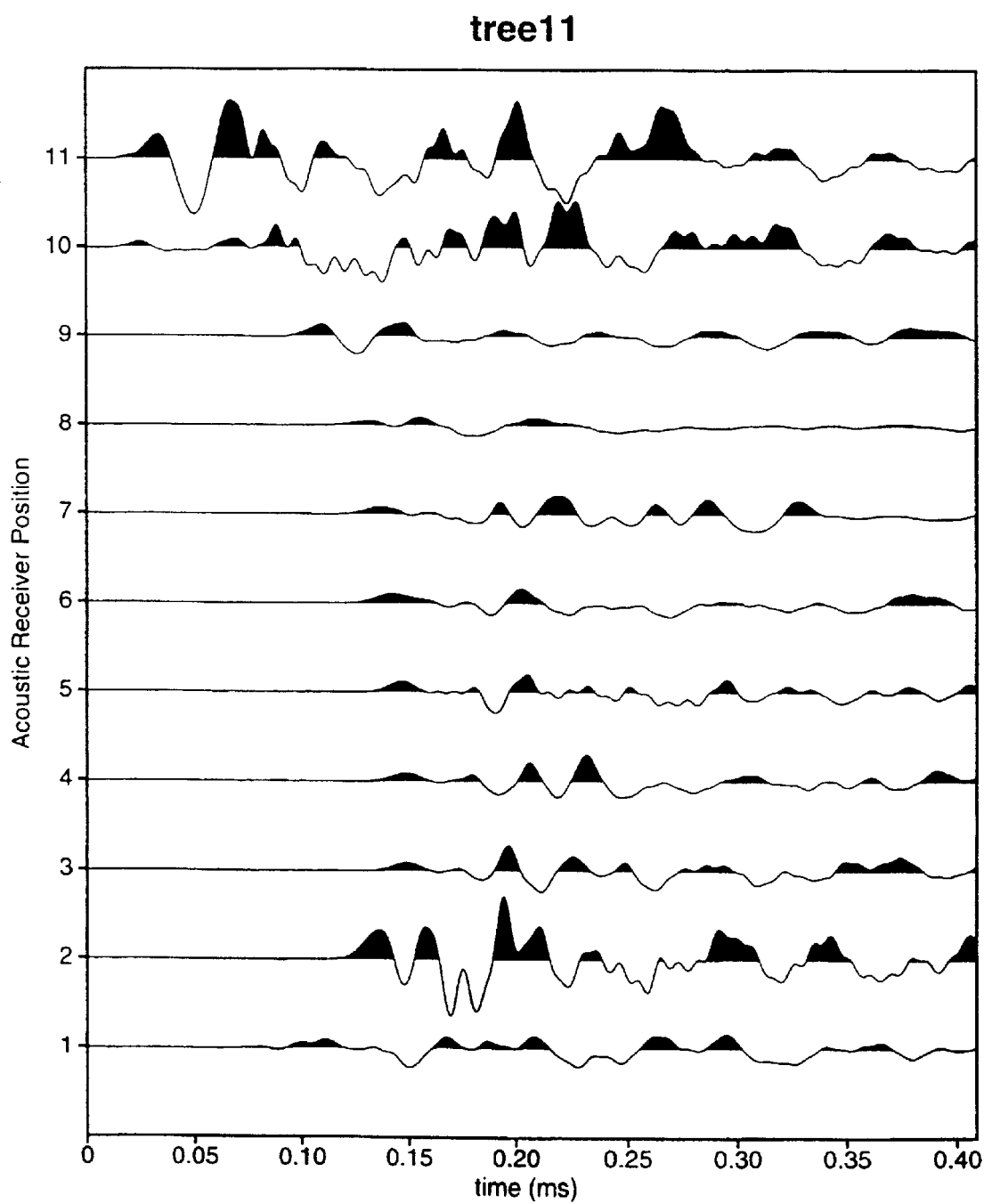
Figure 5L:
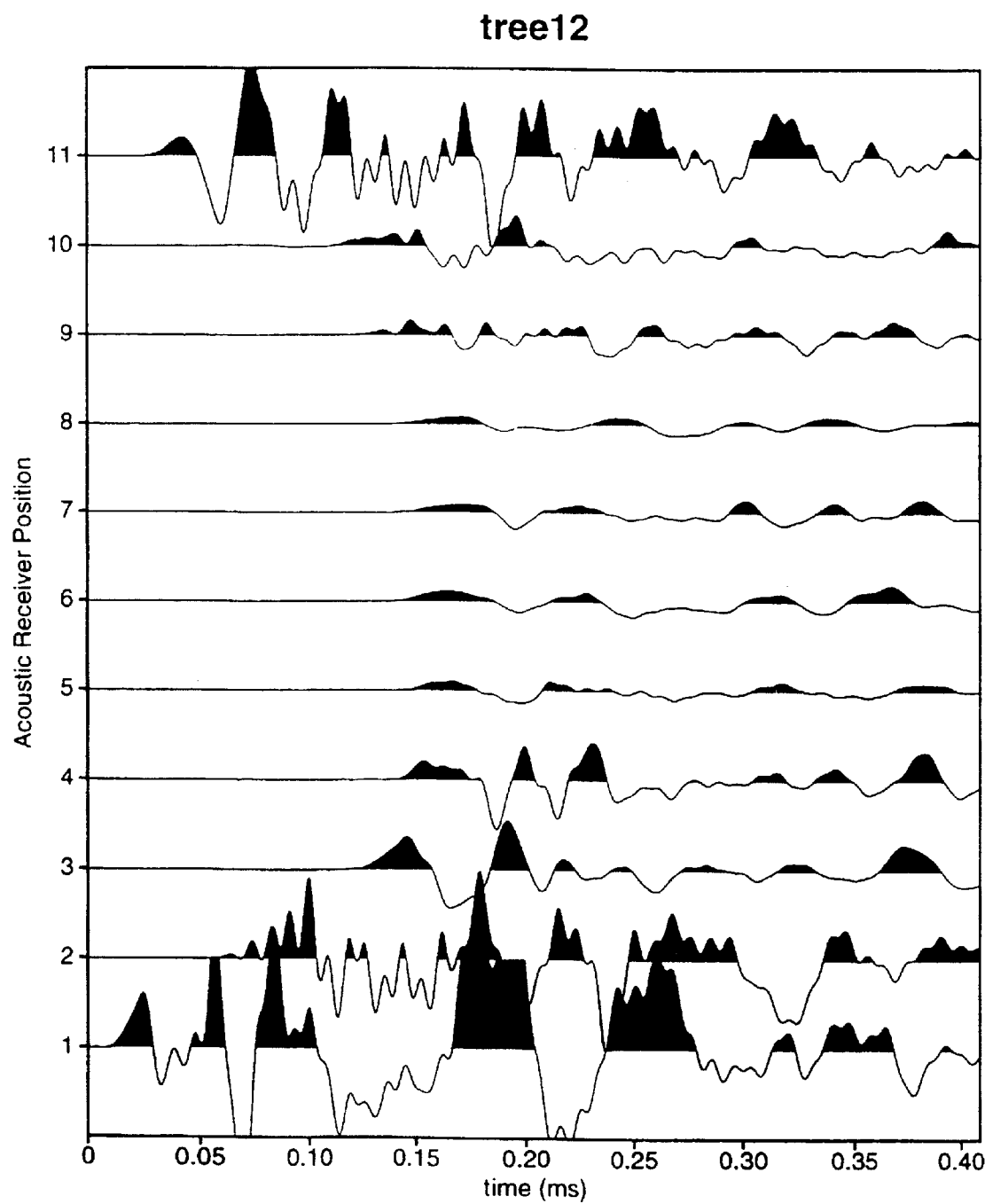
Figure 6A:
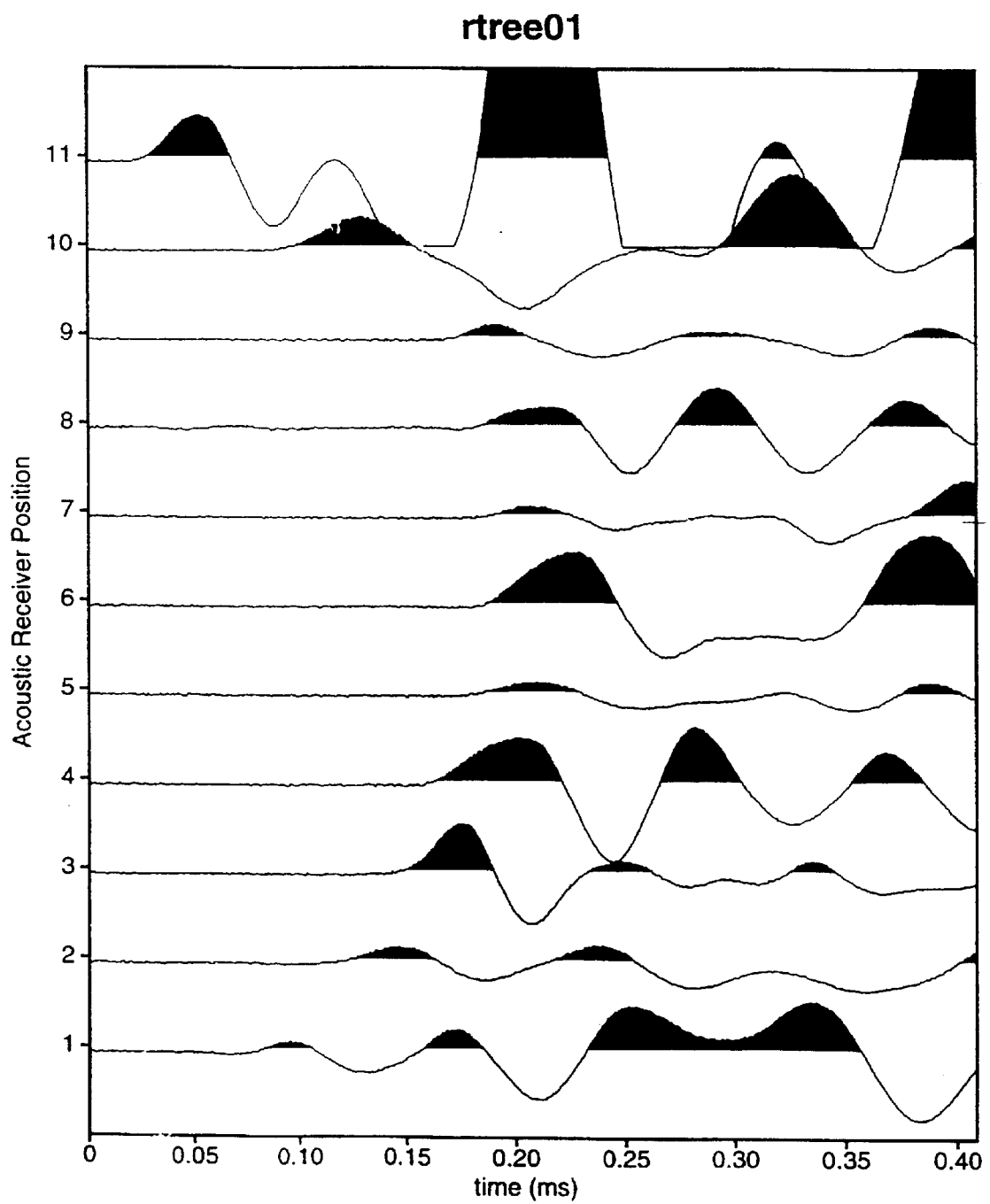
Figure 6B:
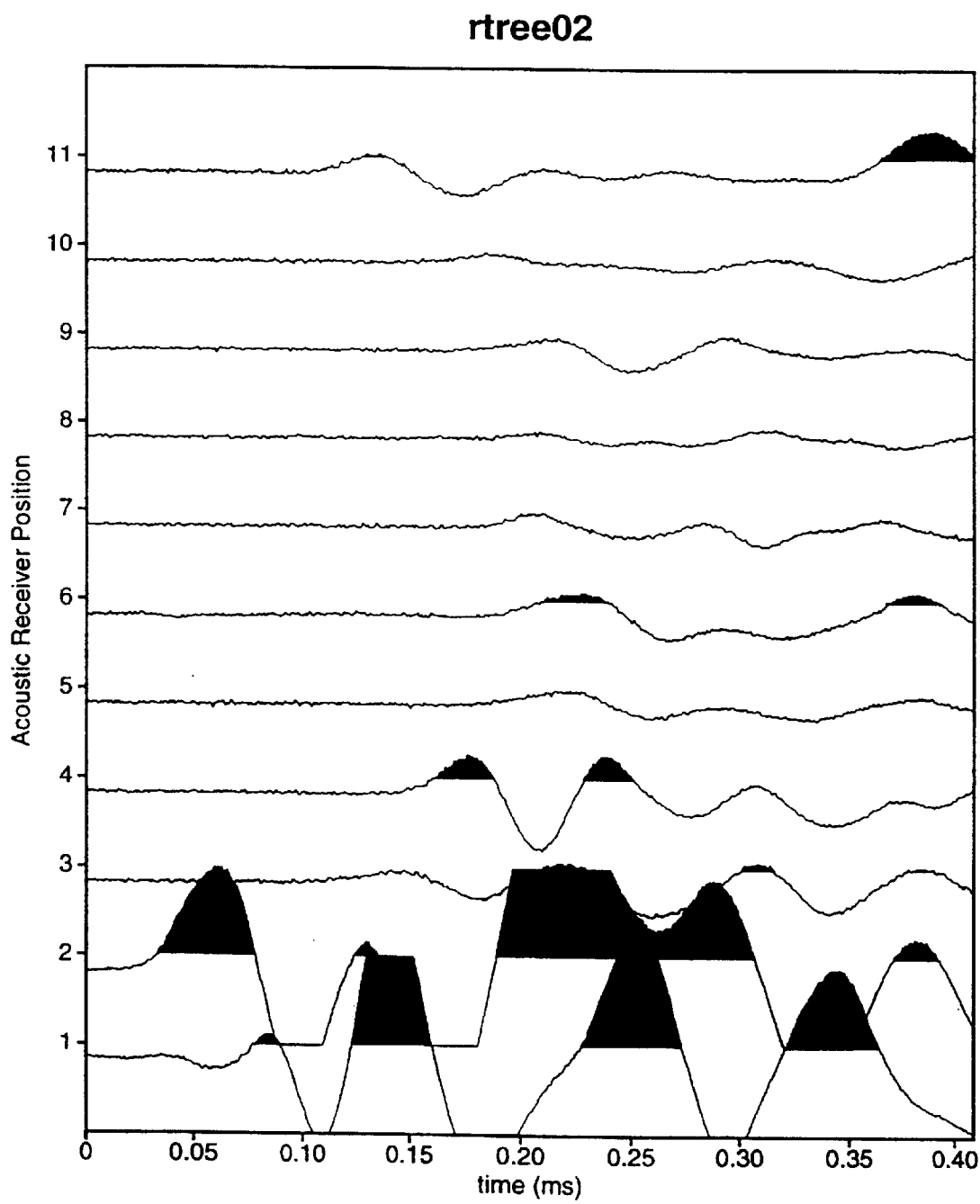
Figure 6C:
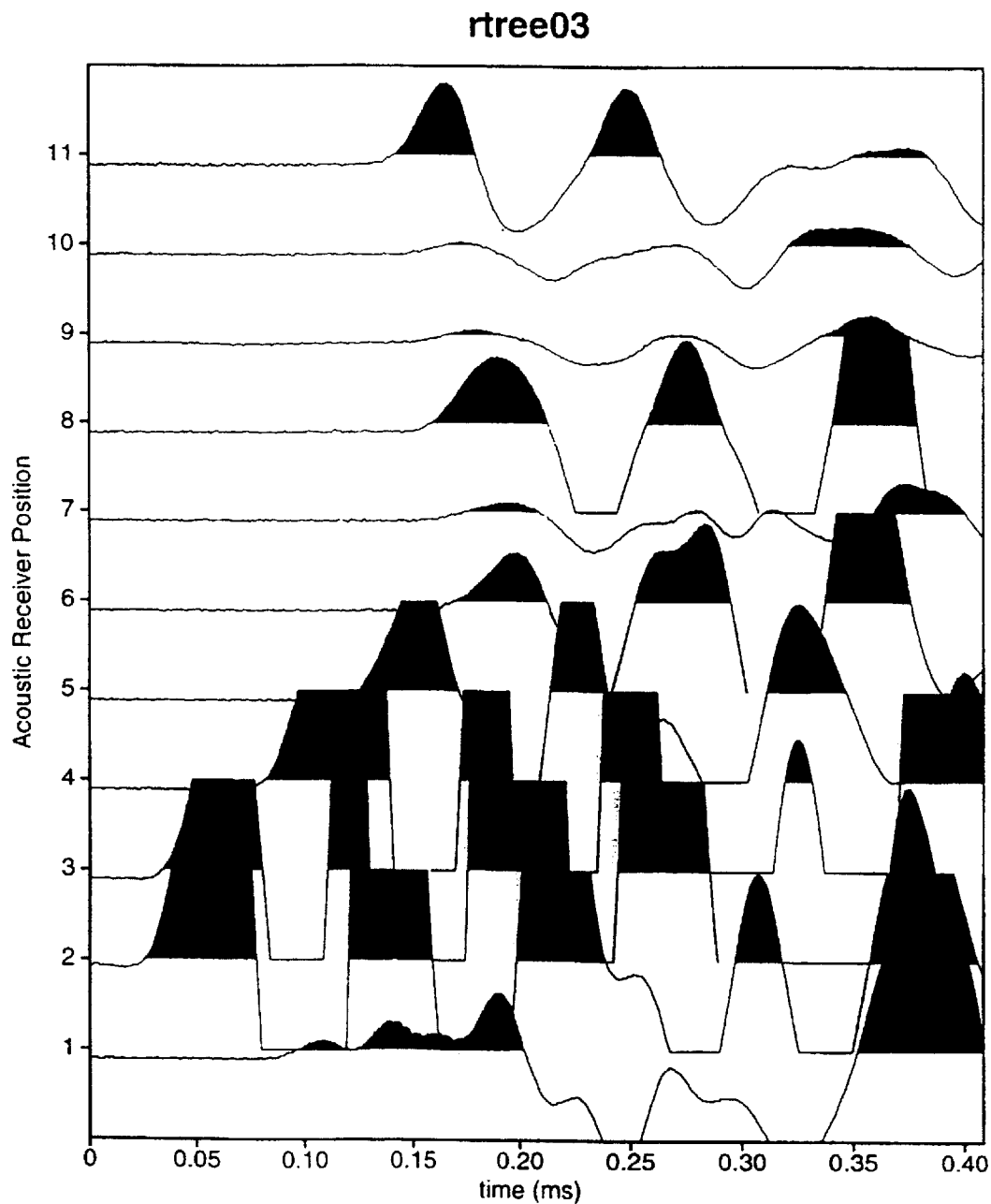
Figure 6D:
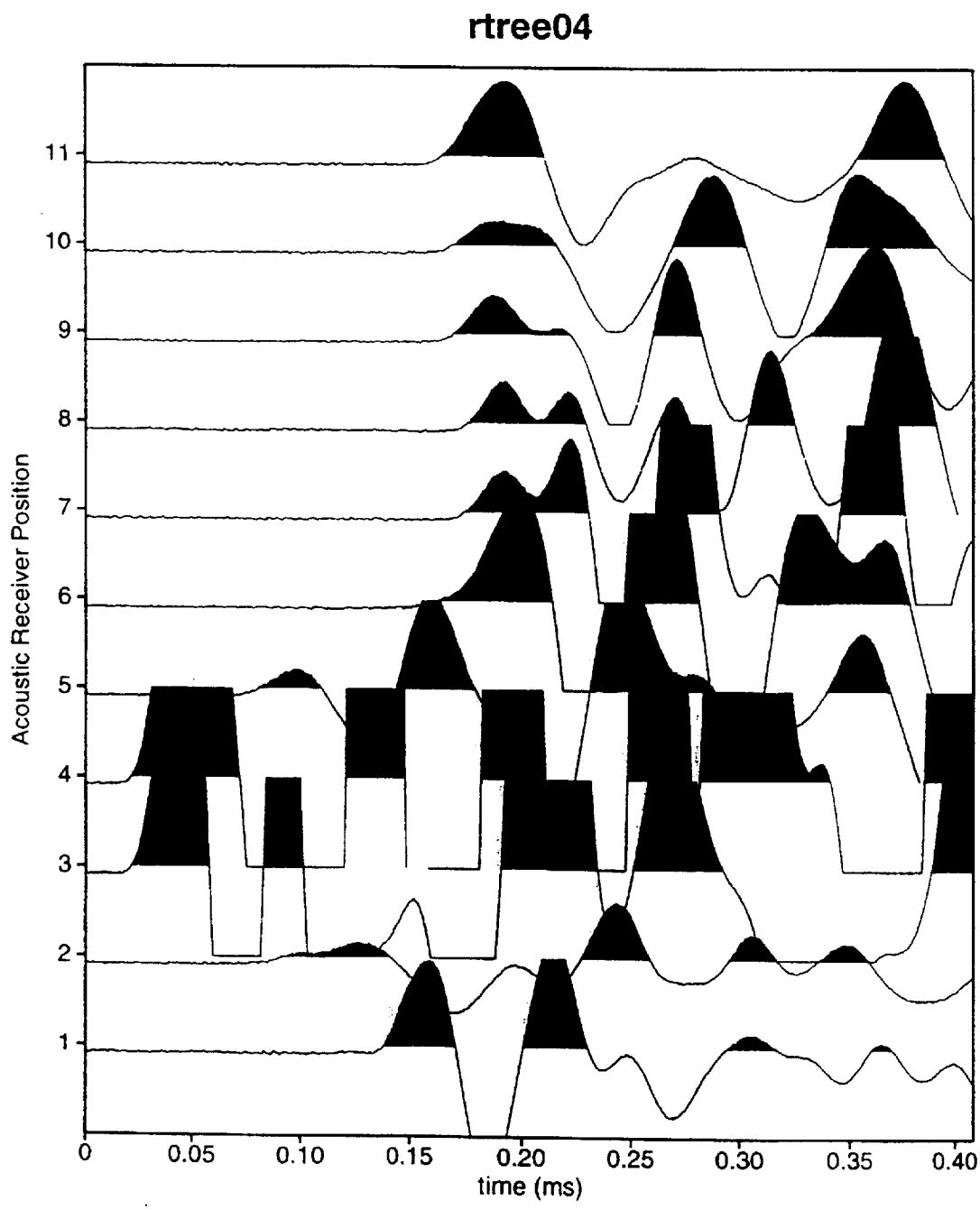
Figure 6E:
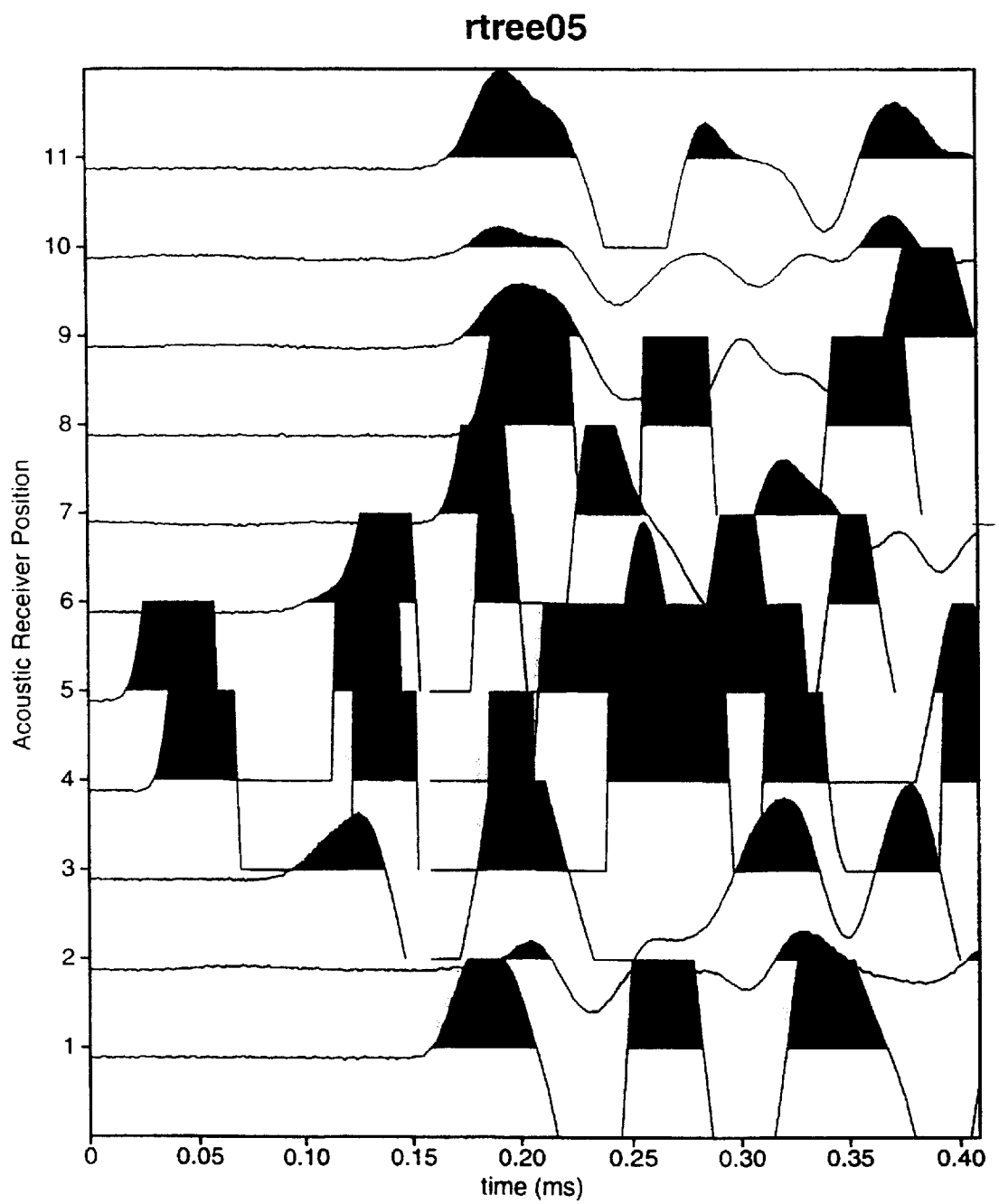
Figure 6F:
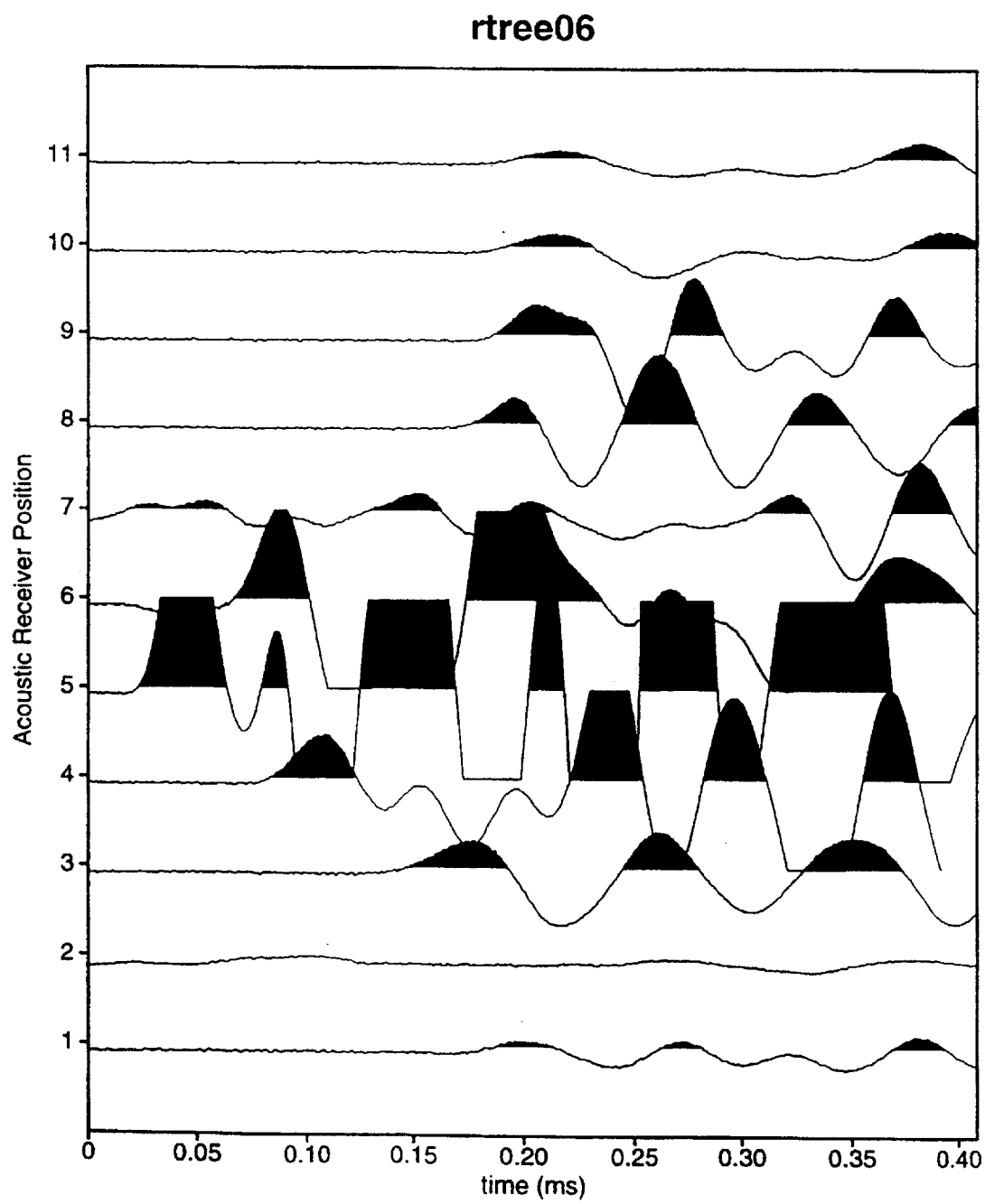
Figure 6G:
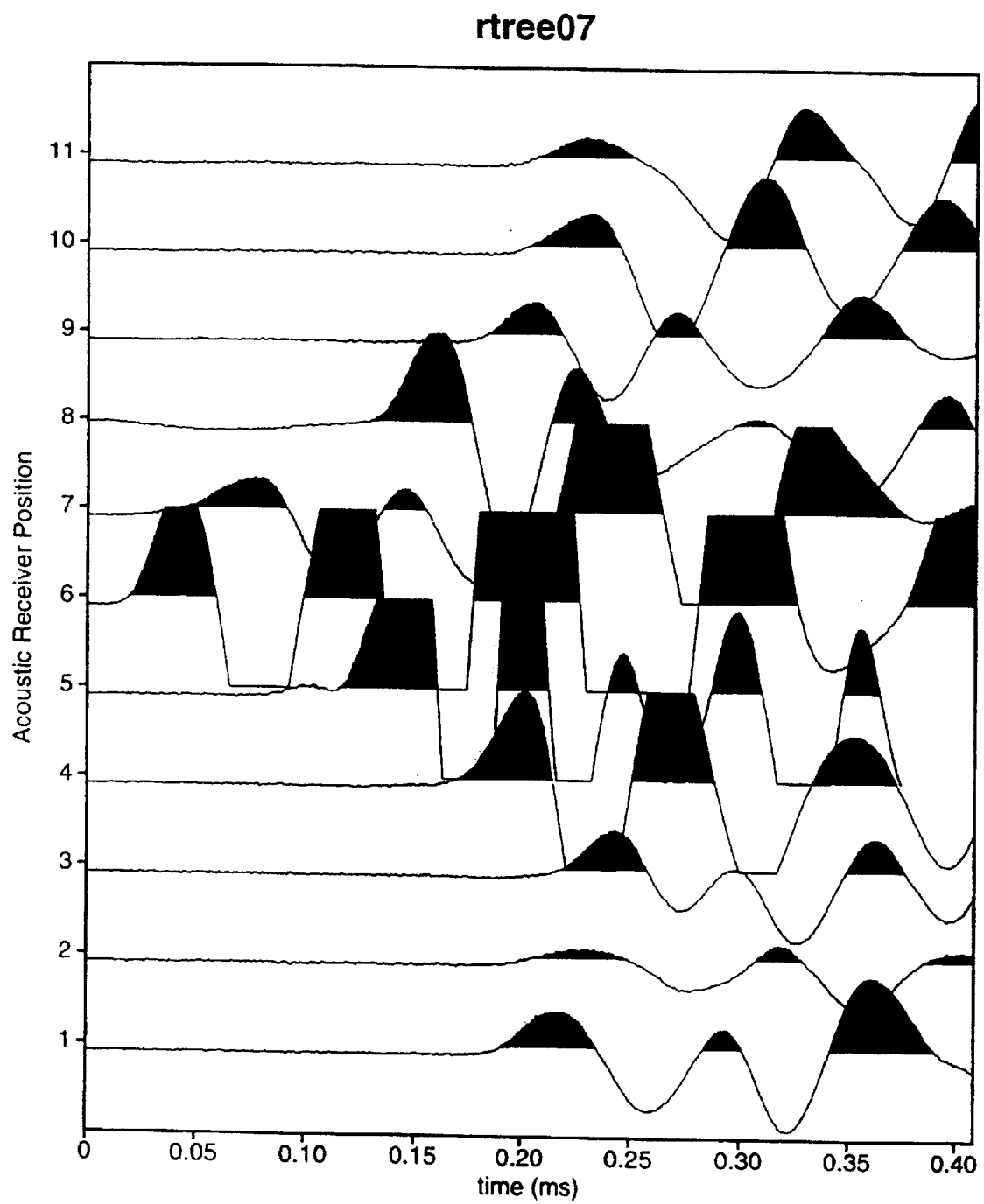
Figure 6H:
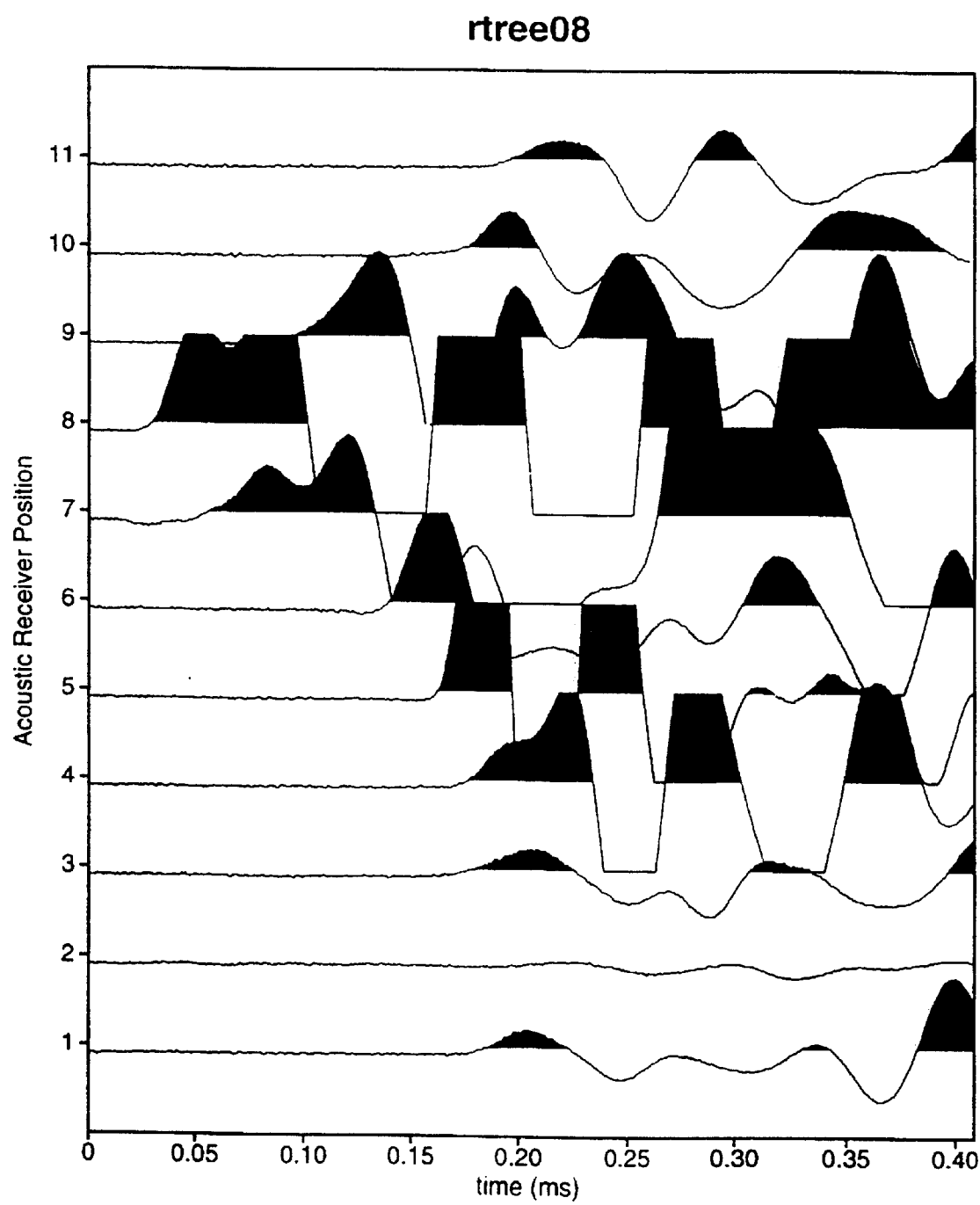
Figure 61:
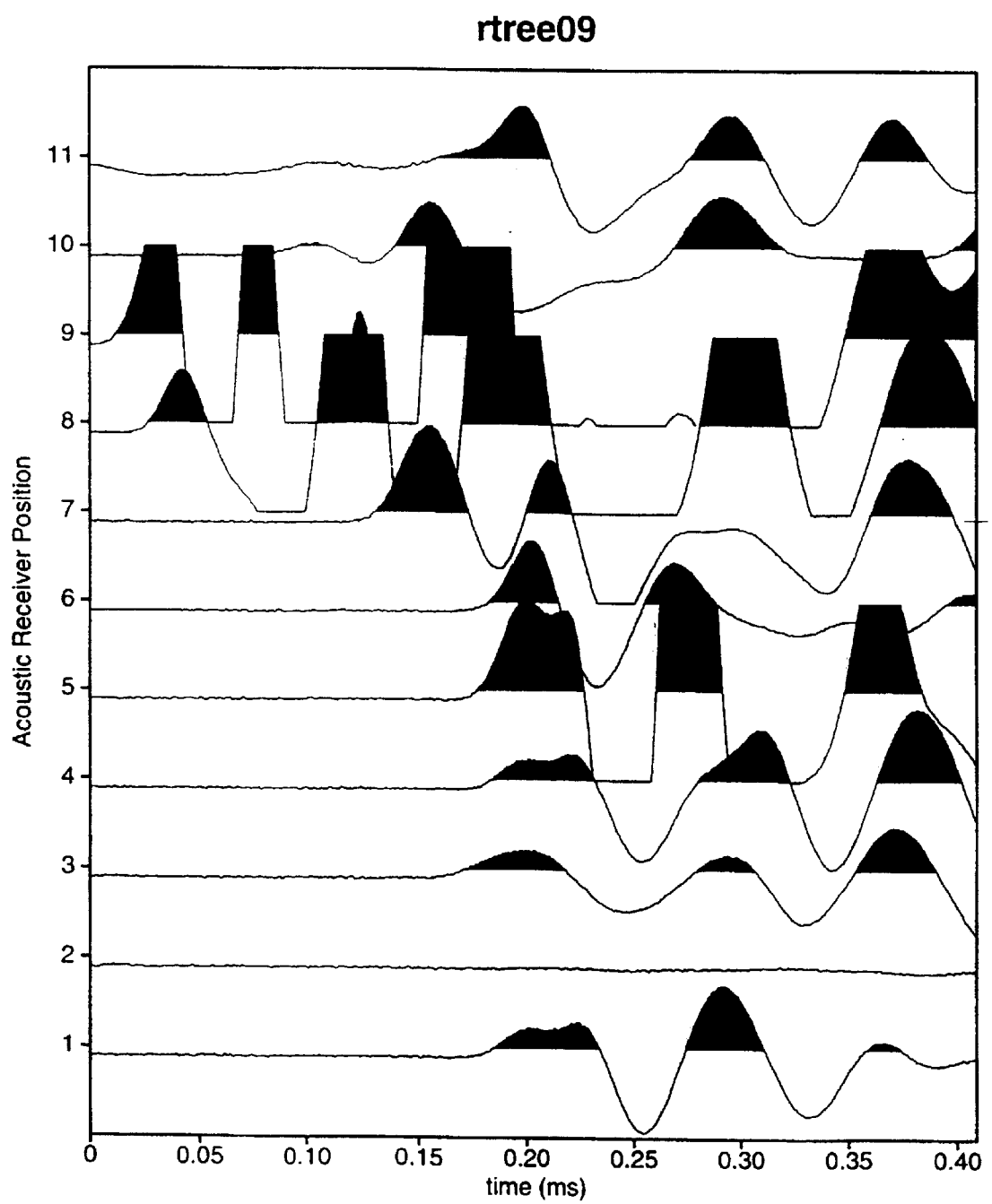
Figure 6J:
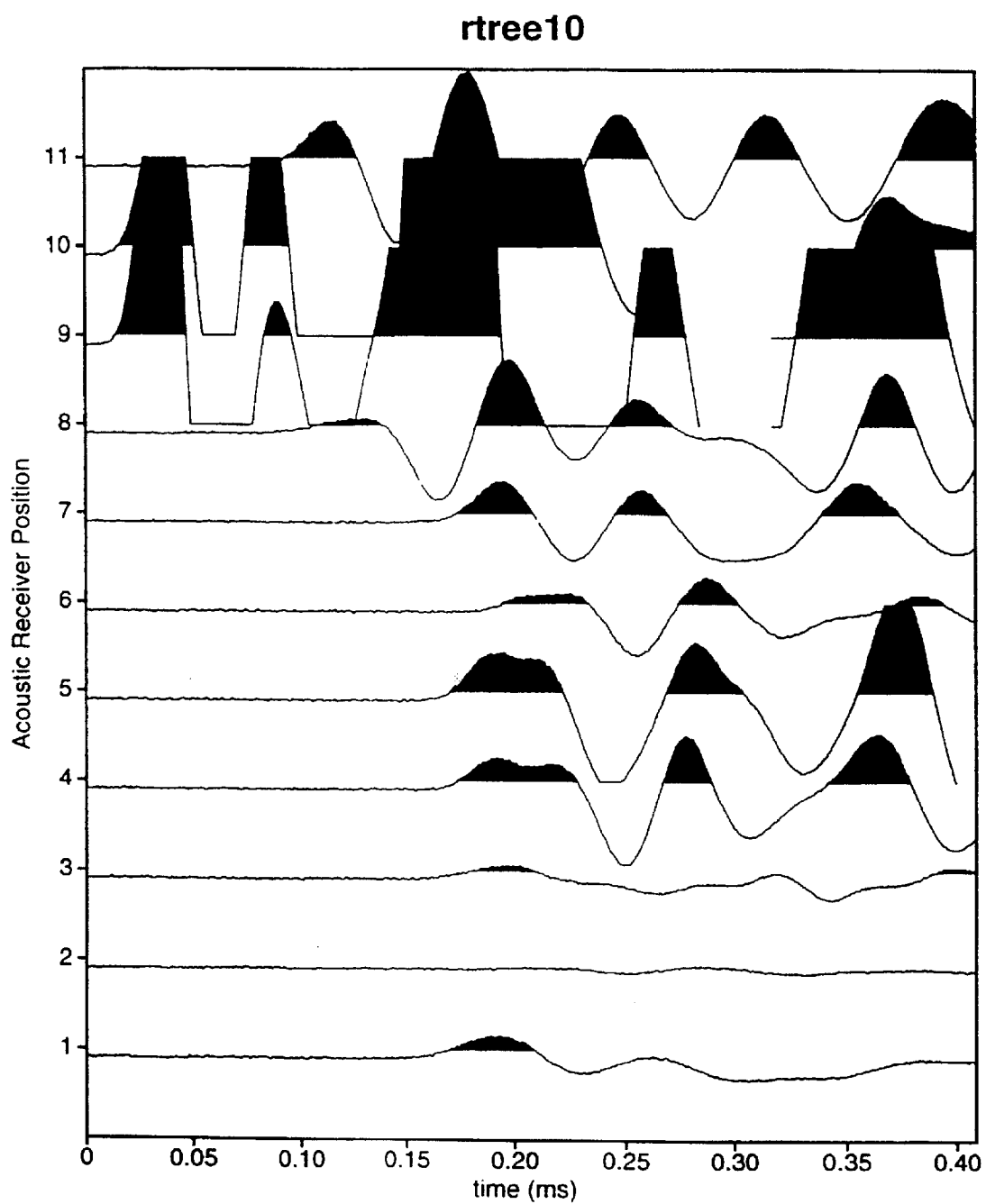
Figure 6K:
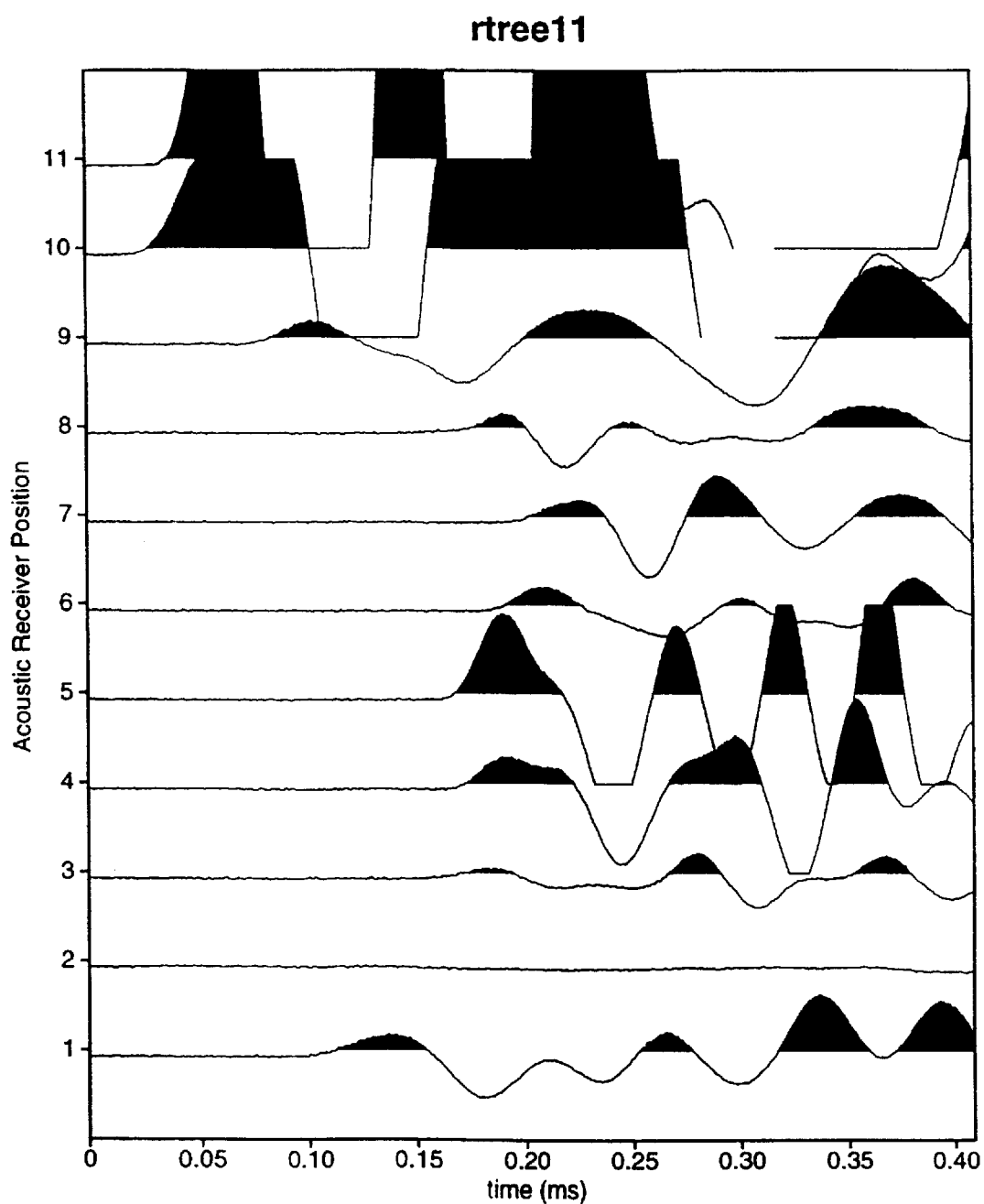
Figure 6L:
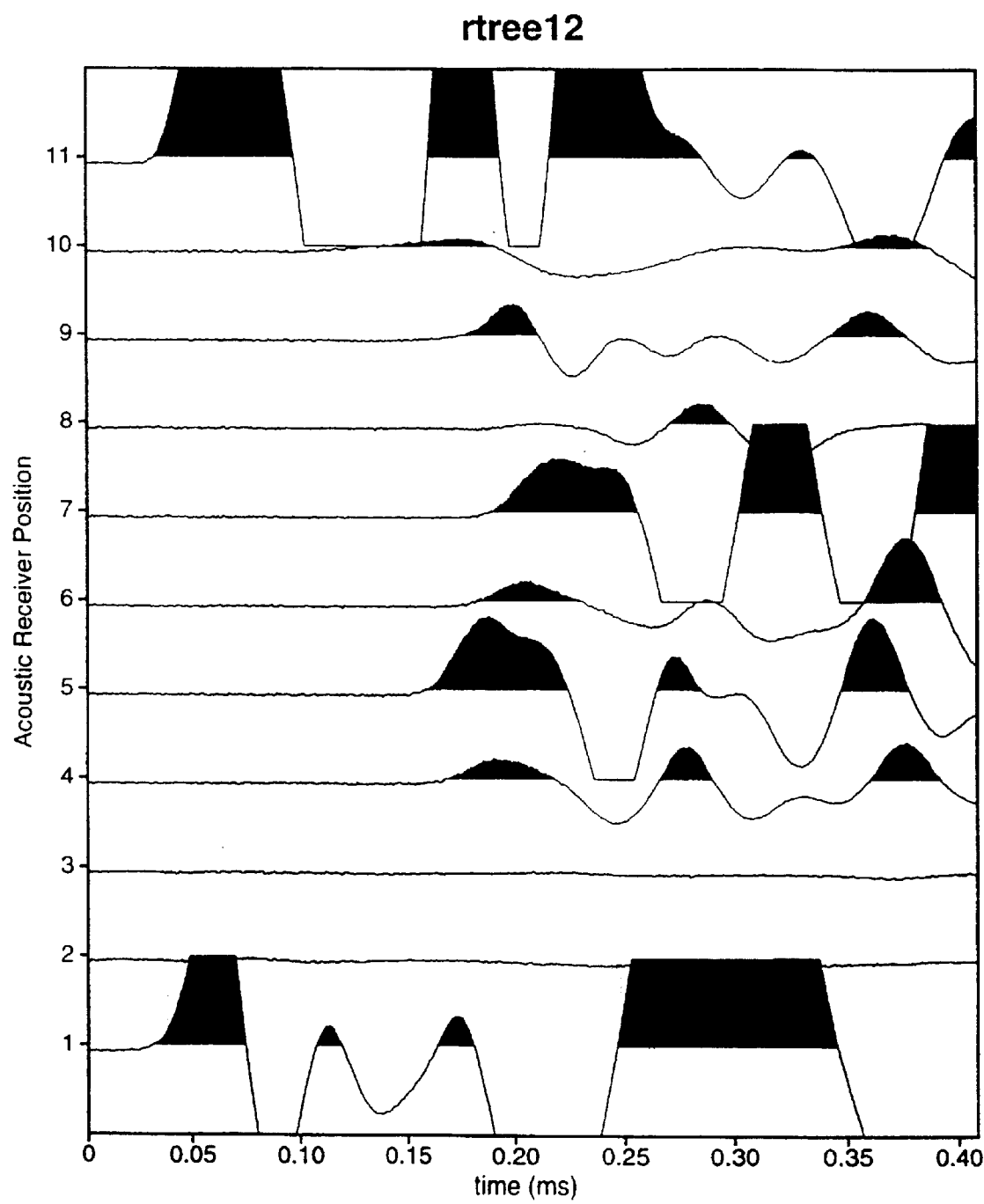
Figure 7:
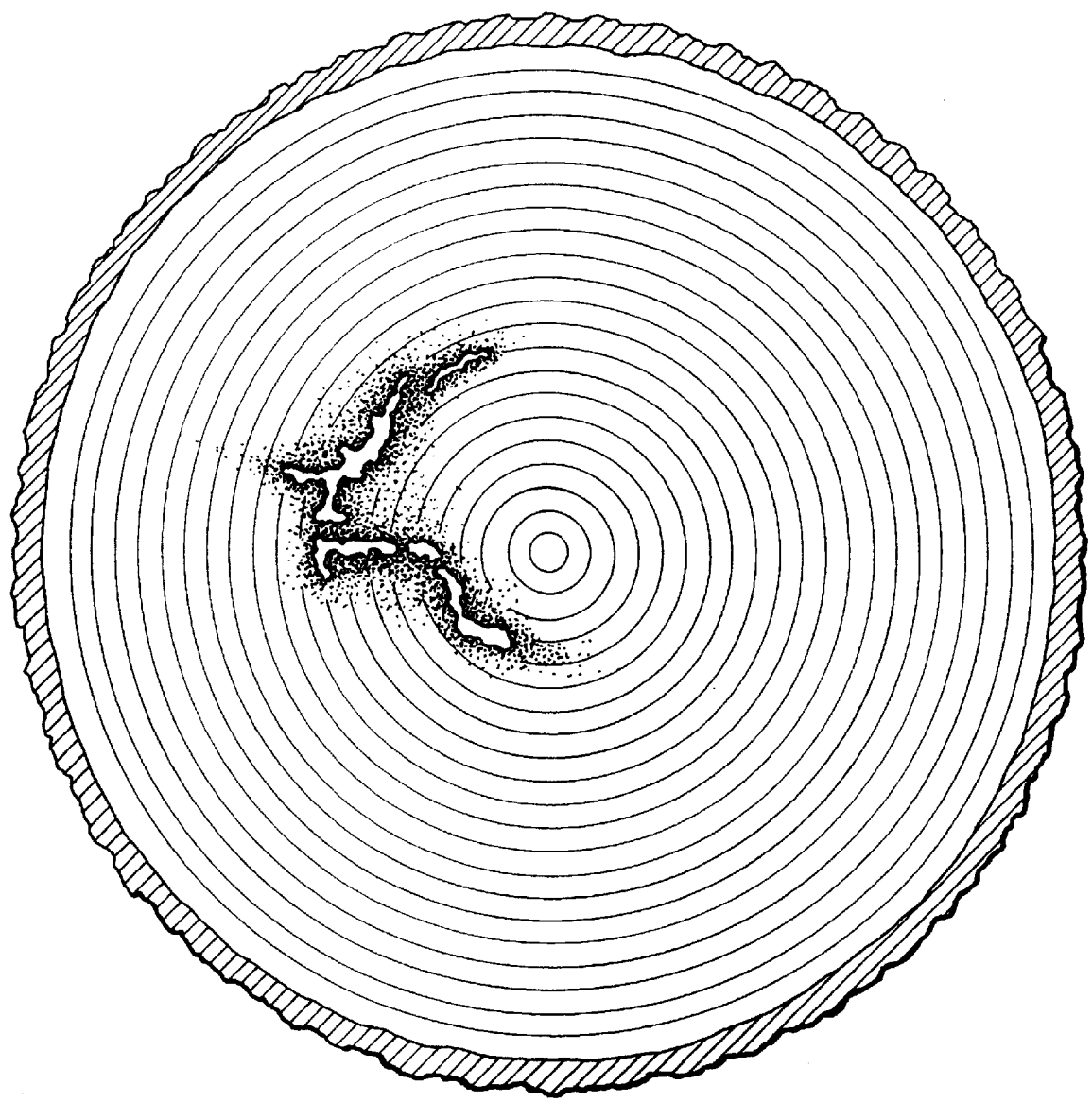
FIG. 7 is a schematic representation of a photograph of a log cut from a tree, showing a type of rotting condition that results in large voids.
Figure 8:
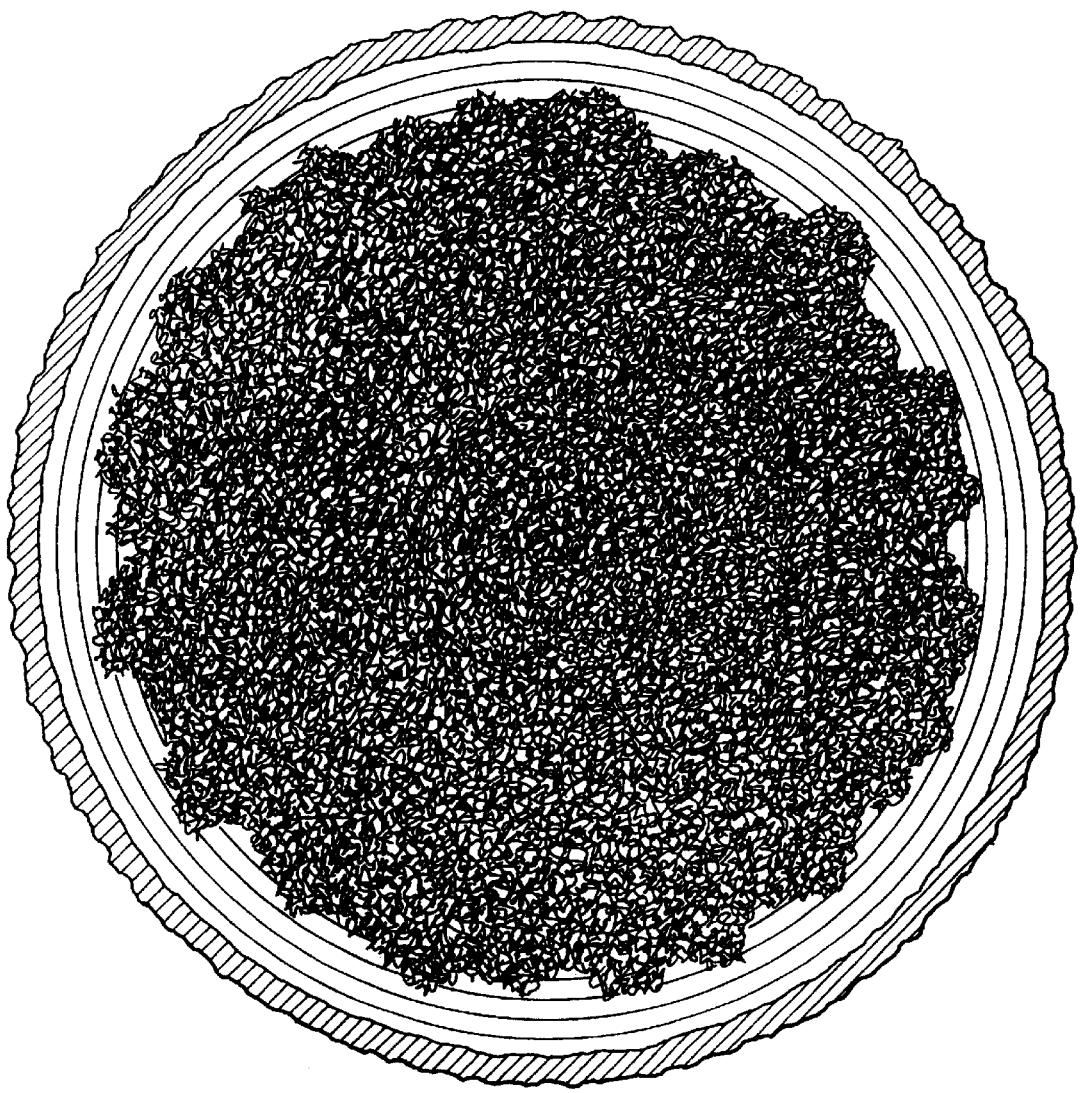
FIG. 8 is a schematic representation of a photograph of a log cut from a tree showing a type of rotting condition that does not result in large voids.

As shown in FIG. 5A, the time of arrival of the first pulse received by the transceiver at position number 11 is about 0.03 ms; at position 10 at 0.1 ms; at position 9 at 0.13 ms; at position 6 at 0.15 ms, and at position 2 at 0.07 ms. FIG. 5C shows the situation with the transceiver between positions number 1 and 2 being the source. Consequently, transceivers that are closer to this location indicate the earliest arrival of the first wave to arrive. Since the time of transmission is known, the time of arrival is also indicative of time of flight ("TOF"). As used herein, time of arrival and TOF are used interchangeably, even though they are not precisely the same.

The transceiver controller steps through each of the transceivers, activating each successive one to be the transmitter for a designated set of measurements. While one transceiver is transmitting, the others are all receiving, and the signals received at each are recorded. After each of the transceivers has functioned as a transmitter, the controller stops causing the transceivers to be energized. (For certain operations, it may be beneficial to step through each of the transceivers a second time, causing them each to act as a transmitter a second time around the circuit.)

Thus, from the data shown in FIGS. 5A–5L, the TOF of an ultrasound pulse through the tree can be determined. Each pulse transmission and reception pair provides a record of the path of shortest duration through the tree. That does not mean that it is the shortest path, from a geometrical, straight line standpoint. This is because sound waves travel all throughout the tree, and the wave that arrives first will have made its way along a path of tree elements (analogous to pixels on a CRT) that permit the fastest travel of sound therethrough. For instance, a tree element that is entirely void will exhibit a sound transmission characteristic similar to that of air. A tree element that is healthy will transmit sound therethrough at a higher velocity. Thus, an ultrasonic pulse that has travelled through a void may take longer to arrive than one that travelled a longer distance, skirting the border of the void.

FIGS. 6A–6L show similar data as FIGS. 5A–5L, but for a tree that includes some rot.

By applying computed tomographic ("CT") techniques to all of the time of first arrival data from each transmitter location to each receiver location, it is possible to generate a two dimensional image of the slice of the tree around which the transceivers are mounted, which image differentiates among different tree elements based on their acoustic transmission properties, showing the tree graded by transmission velocity.

This transmission velocity bears a direct relationship to properties of the tree, such as its density, incompressibility and rigidity, which properties can be correlated to properties that are of interest to the logging, arborial, maintenance, safety and environmental interests outlined above, such as rot, knots, voids and embedded metal spikes.

The tomographic techniques and methods that are applied to the TOF data are similar to those that are used in x-ray tomography. They are also similar to those that were described in work of one of the inventors herein, Matarese, Joseph R., NONLINEAR TRAVELTIME TOMOGRAPHY, a thesis submitted to the Department of Earth, Atmospheric, and Planetary Sciences in partial fulfillment of the requirements for the degree of Doctor of Philosophy in Geophysics, in 1993, the entire disclosure of which is incorporated herein fully by reference.

The Matarese thesis concentrates on using computed tomography (CT) to analyze geological formations, such as the geological conditions around oil wells, and the like. However, with geological formations, it is very difficult to surround the subject with locations of transceivers. To do so requires drilling a well of the desired depth at every location where it is desired to locate a transceiver. In the Matarese thesis, such an arrangement of transceivers is referred to as a "Medical Survey" because of the analogy to medical CT where x-ray transceivers are located all around the patient's body.

Chapters 2, 3 and 4 of the Matarese thesis are of particular interest. Chapter 2 discusses Modeling Traveltimes and Raypaths, focussing on: first arrival traveltimes, traveltime measurement; traveltime modelling, including both raybased and Eikonal Methods, of which ray shooting and two-point perturbation are examples of the former and finite difference, graph-theoretical and extrapolation are examples of the latter. Chapter 2 also discusses Tomographic traveltime modeling, including homogeneous, smoothly-varying, layered and rough models. Chapter 3 discusses reconstructing velocities from traveltimes, particularly the tomography problem, linearized inversion and nonlinear inversion. It is principally the techniques that are outlined in this Ch. 3, that are applied to the time-of-flight data, to reconstruct the velocities at different tree element locations from the traveltimes.

Chapter 4 provides a nonlinear programming approach to traveltime inversion, including raytracing, backprojection, regularization, step length calculation, adding prior information, a numerical solution of the linearized problem, preconditioning, optimization and convergence, and parallel implementation.

It is helpful to have some foreknowledge of the velocity to be expected in the majority of tree elements. However, it is not necessary to have this foreknowledge. If it is available, however, it reduces the number of computational iterations that must be conducted to converge upon a result with certainty. Typically, about 20–30 iterations of the computations are required.

Figure 9:
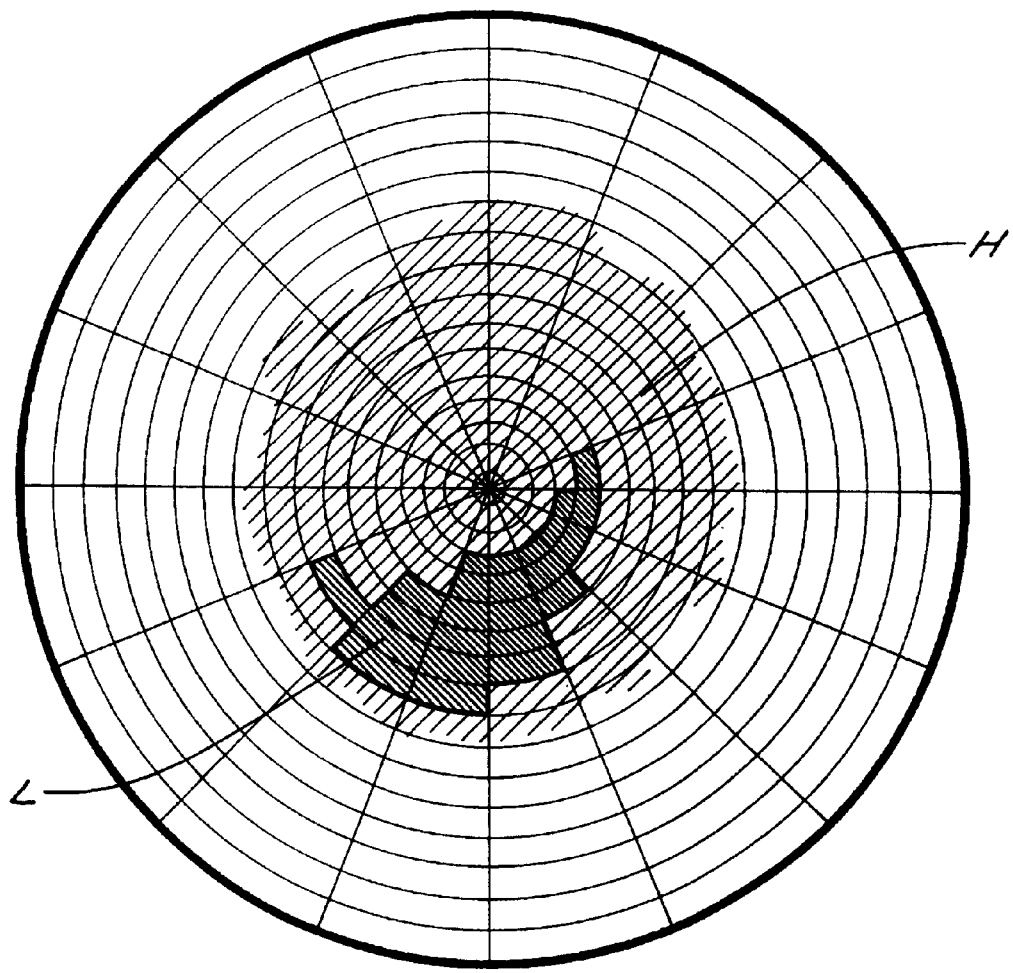
FIG. 9 is a graphical representation of a computed tomographic two dimensional image of the internal structure of a tree, as is generated by an embodiment of the apparatus of the invention.

A schematic rendition of an acoustic tomographic image is shown in FIG. 9. Regions (L) of the tree with lower velocity are differentiated on the controller monitor by color (or shading) from those (H) having higher velocity properties.

It has been found that suitable results can be achieved by using ultrasound pulses in the frequency range of from 15 kHz to 200 kHz, preferably less than 100 kHz. The low end of this range may not be strictly considered to be ultrasound in some circumstances, being within the range of human hearing. However, it is a suitable range for the practice of the present invention. In particular, to detect rotted conditions, it is thought to be important to use relatively lower frequency radiation. The power should be enough to ensure that the ultrasonic energy is transmitted all the way through the tree. However, because the device should be portable and lightweight, it is desireable not to use excessively powerful pulses, because that would result in the use of heavier batteries than is necessary.

It has been found that the moisture content of the wooden member bears upon the power requirements. Generally speaking, moister members, such as standing or recently felled trees, require lower power than do drier members, such as seasoned lumber and utility poles.

The processor should be fast enough and powerful enough such that it can generate an image from twelve sensors in about thirty seconds. Each tree element pixel would be on the order of one square inch in area. This is achievable with technology available in 1998 laptop computers. It is also believed to be possible to be achievable with even smaller computing devices, such as those known as personal digital assistants, or "PDAs", of which the Palm III™, sold by 3Com, is a representative type. In some cases, the PDA may need additional memory, over its standard complement.

It is also possible to analyze waves that arrive after the first arrivals (which later waves typically include surface waves) to identify the location of any object (such as metal spikes) that is near the surface. These are waves, such as shown in FIGS. 5A–5L, that arrive after the first few waves to arrive.

ENERGY ATTENUATION

The foregoing discussion has focussed on generating two dimensional images that correspond to the velocity characteristics of the different elements of the tree. It is also beneficial to take into account the energy attenuation characteristics of the different tree elements. This can also be done with computed tomography techniques. It will be observed that the traces shown in FIGS. 5A–L and 6A–L show not only the time of arrival of the first wave to arrive at each transceiver, but also the amplitude of each such first arriving wave. With knowledge of the amplitude of the transmitted pulse, the attenuation of each first arriving wave can be determined.

Using the same types of calculations and techniques as were used to compute the velocity characteristics of the tree elements, the energy attenuating properties of the tree elements can also be determined. It is most convenient to conduct the energy attenuation analysis after the velocity analysis, because the velocity analysis identifies the paths that the first arriving pulses actually follow. Knowing these paths, the tree elements that are responsible for the various degrees of energy attenuation can be identified.

It is believed that the effect of tree condition on energy attenuation is more severe than the effect of tree condition on velocity variation. Thus, the image that is derived at least in part from the velocity attenuation analysis is believed to provide a more sensitive, and detailed image. It is possible to generate an image based only on the attenuation information, or on a combination of the attenuation and the velocity information.

CHARACTERISTICS OF THE BELT

The belt 102 that carries the transceivers, battery power supply and the other components should satisfy several criteria. It should be able to be tightened to a significant degree. This can be accomplished by many different types of clamping apparati, such as a levered hook, similar to an oil filter wrench; a small motor that cinches the strap tight; a hydraulic cylinder. During tightening, the belt should not stretch. This is because it is important, for purposes of the tomographic techniques, to know with precision the distance between transceivers. Thus, it is beneficial to construct the belt from a lightweight, stretch resistant material, such as Kevlar™ brand fibers (sold by Du Pont) or carbon fibers. Kevlar™ brand and carbon fibers also have the advantage of being lightweight and very strong.

The belt should also not transmit ultrasonic vibration through itself, but rather should damp out the transmission of any such vibration. This is to insure that the vibration received by the transceivers has traveled through the tree, rather than around the tree, through the belt. Any such "cross-talk" would be undesireable. Thus, the belt can include vibration damping links in between the transceiver links.

The belt also typically carries a plurality of radar pulse generators 122 and radar receivers 124. (Only one of each is shown. These components would be equally spaced around the perimeter of the tree.) These are used to determine the true diameter of the tree, in the case that the tree perimeter is not circular. The radar operation is by transmission, not reflection.

THREE DIMENSIONAL IMAGE

Figure 4:
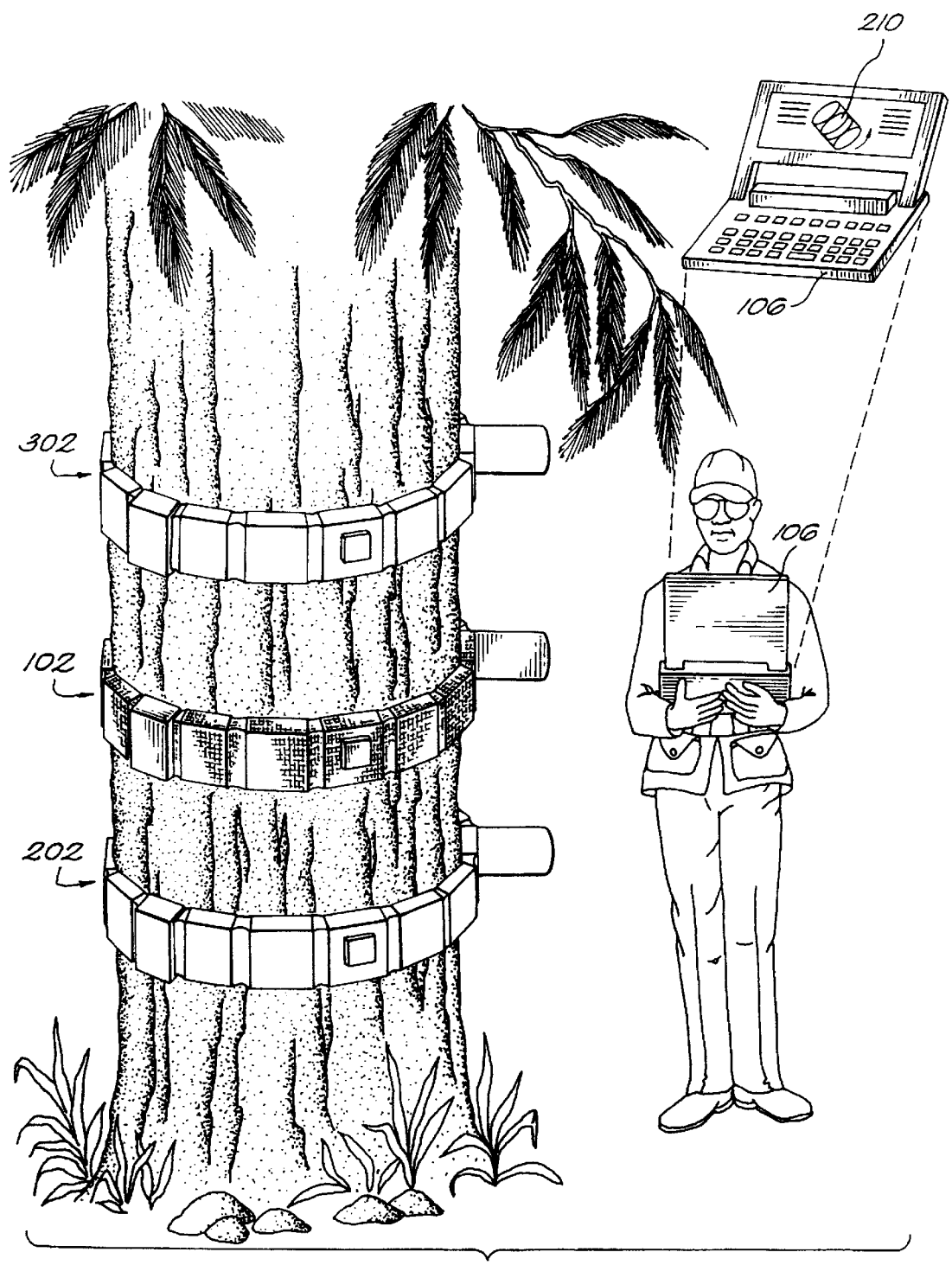
FIG. 4 is a schematic view of an embodiment of an apparatus of the invention, with three transceiver belts, as shown in FIG. 2, engaged around a tree, for generating a three-dimensional image of the internal structure of the tree.

The foregoing discussion has described an apparatus that generates an image of a two-dimensional slice surface of a tree. FIG. 4 shows an apparatus that generates a three-dimensional image of a block of tree, for instance six feet in length. This embodiment employs three (or more) belts 102, 202 and 302, each substantially identical to the belt 102 that is discussed above. The operation is essentially the same, except that the process traverses through using each of the transceivers on each of the three belts as a transmitter. For each momentary transmitter, the first signal to arrive is noted at each of the other transceivers in the belt in which the transmitter resides, and, in the other two (or more) belts.

The same computed tomography techniques that are set forth in the Matarese thesis that were mentioned above in connection with the two dimensional embodiment can be applied in the three dimensional case with only a little more complexity due to the additional transceivers, and the added geometrical dimension. The result of these techniques is a three dimensional image 210 of a cylindrical portion of the tree, each level of which can be imaged as a two-dimensional slice. Such a three dimensional image can be rotated around any axis to view from any angle, and can be sliced for a two dimensional image by any plane, as is common with current computer aided design and medical imaging packages Thus, a three dimensional image may be garnered. This embodiment may be particularly useful for orienting logs during mill operation, and also for locating embedded objects, such as spikes inserted by those seeking to limit logging activity. This is because the spikes are relatively small, and the scope of examination is expanded by quite a bit when three belts are used. When one belt is used, a slice of tree on the order of a few inches thick is examined. When three belts are used, a slice on the order of four to six feet thick can be examined. Thus, by increasing the weight of the apparatus by three, its field of examination is increased on the order of twenty fold.

The invention may be used with very large trees, such as Sitka spruce, Douglas firs, and redwoods, which may be as large as ten feet in diameter.

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

In particular, the invention can also be used to examine all types of wooden members, such as utility poles, including telephone poles, piers, dock supports, scaffolding, and pilings.

The corresponding structures, materials, acts and equivalents of all means or step plus function elements in the claims below are intended to include any structure, material, or acts for performing the functions in combination with other claimed elements as specifically claimed.

Having described the invention, what is claimed is:

1. An ultrasound apparatus for determining the internal condition of a wooden member, said apparatus comprising:
   a. a belt, sized to encircle a wooden member to be examined, which belt carries:
      i. a plurality of ultrasonic transceivers, spaced along said belt; and
      ii. a tightening mechanism that enables said belt to be tightened around said wooden member;
   b. a controller configured to:
      i. energize selected of said transceivers to transmit ultrasound energy, and others of said transceivers to receive said ultrasound energy;
      ii. receive signals that are based on said transmitted energy and said received energy; and
      iii. analyze said received signals to generate a signal that corresponds to the condition of a two dimensional slice surface of said wooden member; and
   c. a signal channel that couples said transceivers to said controller.

2. The ultrasound apparatus of claim 1, said controller configured to identify at each receiving transceiver, a first signal to arrive that has been transmitted from a given transmitting transceiver, and to identify the time of arrival of said first signal to arrive, and, based on analyzing said times of arrival of said first signal to arrive at each receiving transceiver, generating said signal that corresponds to the condition of said two dimensional slice surface of said wooden member.

3. The ultrasound apparatus of claim 1, said controller configured to compare, at each receiving transceiver, an amplitude of a first signal to arrive that has been transmitted from a given transmitting transceiver, with an amplitude of a corresponding signal that has been transmitted by said given transmitting transceiver, and, based on analyzing said comparison of amplitudes, and any attenuation therebetween, generating said signal that corresponds to the condition of said two dimensional slice surface of said wooden member.

4. The ultrasound apparatus of claim 2, said controller configured to compare, at each receiving transceiver, an amplitude of said first signal to arrive that has been transmitted from a given transmitting transceiver, with an amplitude of a corresponding signal that has been transmitted by said given transmitting transceiver, and, based on analyzing said comparison of amplitudes, and any attenuation therebetween, as well as said times of arrival of said first signal to arrive, generating said signal that corresponds to the condition of said two dimensional slice of said wooden member.

5. The ultrasound apparatus of claim 1, said transceivers each comprising a member engagement tooth, designed to couple acoustic energy between said transceiver and a wooden member.

6. The ultrasound apparatus of claim 5, said tooth comprising a spike.

7. The ultrasound apparatus of claim 5, said tooth comprising a cup.

8. The ultrasound apparatus of claim 1, further comprising, carried upon said belt, at least one radar transmitter and a paired radar receiver, and means for coupling said radar transmitter and receiver to said controller, said controller further being configured to analyze signals received at said radar receiver to determine the relative positions of said ultrasound transceivers.

9. The ultrasound apparatus of claim 1, said controller configured to apply computer aided tomographic (CAT) techniques to analyze said received signals to generate said signal that corresponds to the condition of a two dimensional slice surface of said wooden member.

10. The ultrasound apparatus of claim 1, said signal channel that couples said transceivers to said controller comprising an infra-red frequency band channel.

11. The ultrasound apparatus of claim 1, said plurality of transceivers numbering at least ten.

12. The ultrasound apparatus of claim 1, further comprising:
   a. a second belt, sized to encircle said wooden member to be examined, which second belt carries:
      i. a second plurality of ultrasonic transceivers, spaced along said belt; and
      ii. a tightening mechanism that enables said belt to be tightened around said wooden member;
   b. a signal channel that couples said second plurality of transceivers to said controller; and
   c. said controller further being configured to:
      i. energize said second plurality of transceivers to receive said ultrasound energy transmitted by said selected transceivers of said first plurality;
      ii. energize selected of said second plurality of transceivers to transmit ultrasound energy, and others of said second plurality of transceivers to receive said ultrasound energy transmitted by selected of said second plurality of transceivers;
      iii. energize said first plurality of transceivers to receive said ultrasound energy transmitted by said selected transceivers of said second plurality;
      iv. receive signals that are based on said transmitted energy and said received energy at said second plurality of transceivers; and
      v. analyze said received signals from said first and second plurality of transceivers to generate a signal that corresponds to the condition of a three dimensional volume of said wooden member.

13. The ultrasound apparatus of claim 12, further comprising:
   a. a third belt, sized to encircle said wooden member to be examined, which third belt carries:
      i. a third plurality of ultrasonic transceivers, spaced along said belt; and
      ii. a tightening mechanism that enables said third belt to be tightened around said wooden member;
   b. a signal channel that couples said third plurality of transceivers to said controller; and
   c. said controller further being configured to:
      i. energize said third plurality of transceivers to receive said ultrasound energy transmitted by said selected transceivers of said first and second pluralities;
      ii. energize selected of said third plurality of transceivers to transmit ultrasound energy, and others of said third plurality of transceivers to receive said ultrasound energy transmitted by selected of said third plurality of transceivers;
      iii. energize said first and second pluralities of transceivers to receive said ultrasound energy transmitted by said selected transceivers of said third plurality;
      iv. receive signals that are based on said transmitted energy and said received energy at said third plurality of transceivers; and v. analyze said received signals from said first and second and third pluralities of transceivers to generate a signal that corresponds to the condition of a three dimensional volume of said wooden member.

14. The ultrasound apparatus of claim 1, said belt comprising a material that does not stretch under the tension required to secure it to a wooden member and acoustically couple said transceivers to said wooden member.

15. The ultrasound apparatus of claim 14, said belt comprising fibers selected from the group consisting of Kevlar™ and carbon.

16. The ultrasound apparatus of claim 1, further comprising a battery unit, carried by said belt, which battery unit provides power to said transceivers.

17. The ultrasound apparatus of claim 1, said belt sized to encircle a tree.

18. The ultrasound apparatus of claim 1, said belt sized to encircle a utility pole.

19. The ultrasound apparatus of claim 1, further comprising a device that generates a human perceptible signal that corresponds to the condition of a two dimensional slice surface of said wooden member.

20. The ultrasound apparatus of claim 1, said belt comprising acoustic energy attenuation material, that impedes the transmission of acoustic energy from any transceiver, through said belt, to any other transceiver.

21. A method for determining the internal condition of a wooden member, said method comprising the steps of:
   a. acoustically coupling a first plurality of ultrasonic transceivers to a wooden member, around its circumference, said transceivers carried by a removable belt;
   b. causing each of said transceivers, in a known order, to generate acoustic energy that is coupled into said wooden member, and that is received by each other of said transceivers;
   c. transmitting, to a control unit, signals that correspond to said received acoustic energy;
   d. in said control unit, determining, for each transmitting transceiver, times of arrival at each receiving transceiver of the first acoustic pulse to arrive; and
   e. based on said times of arrival, generating a signal that corresponds to the condition of a two dimensional slice surface of said wooden member.

22. The method of claim 21, said step of generating a signal comprising the step of using computer aided tomographic techniques to generate said signal that corresponds to the condition of a two dimensional slice surface of said wooden member.

23. The method of claim 22, further comprising the steps of:
   a. in said control unit, determining, for each transmitter, amplitude attenuation at each receiver of the first acoustic pulse to arrive; and
   b. based on said attenuation and said time of arrival, generating a signal that corresponds to the condition of a two dimensional slice surface of said wooden member.

24. The method of claim 21, further comprising the step of displaying on a human perceptible display, said signal that corresponds to the condition of a two dimensional slice surface of said wooden member.

25. The method of claim 21, further comprising:
   a. acoustically coupling a second plurality of ultrasonic transceivers to said wooden member, around its circumference, said second plurality of transceivers carried by a second removable belt;
   b. causing each of said second plurality of transceivers to receive said acoustic energy that has been transmitted by said first plurality of transceivers;
   c. causing each of said second plurality of transceivers, in a known order, to generate acoustic energy that is coupled into said wooden member, and that is received by each other of said second plurality of transceivers;
   d. causing each of said first plurality of transceivers to receive said acoustic energy that has been transmitted by said second plurality of transceivers;
   e. transmitting, to said control unit, signals that correspond to said received acoustic energy, received at said first and said second plurality of transceivers;
   f. in said control unit, determining, for each transmitting transceiver, times of arrival at each receiving transceiver of the first acoustic pulse to arrive; and
   g. based said times of arrival, generating a signal that corresponds to the condition of a three dimensional volume of said wooden member.

26. The method of claim 21, further comprising the step of transmitting radar signals from a first location on said belt, and receiving said radar signals at a second location on said belt, and using said received radar signals to determine the relative positions of said ultrasound transceivers.

27. The method of claim 21, said step of coupling a first plurality of ultrasonic transceivers to a wooden member comprising the step of coupling said transceivers to a standing tree.

28. The method of claim 21, said step of coupling a first plurality of ultrasonic transceivers to a wooden member comprising the step of coupling said transceivers to a felled tree.

29. The method of claim 21, said step of coupling a first plurality of ultrasonic transceivers to a wooden member comprising the step of coupling said transceivers to a utility pole.

30. The method of claim 25, said step of generating a signal comprising the step of using computer aided tomographic techniques to generate said signal that corresponds to the condition of a three dimensional volume of said wooden member.

31. A method for determining the internal condition of a wooden member, said method comprising the steps of:
   a. acoustically coupling a first plurality of ultrasonic transceivers to a wooden member, around its circumference, said transceivers carried by a removable belt;
   b. causing each of said transceivers, in a known order, to generate acoustic energy that is coupled into said wooden member, and that is received by each other of said transceivers;
   c. transmitting, to a control unit, signals that correspond to said received acoustic energy;
   d. in said control unit, identifying, for each transmitting transceiver, a feature of acoustic energy arrival at each receiving transceiver; and
   e. based on said feature, generating a signal that corresponds to the condition of a two dimensional slice surface of said wooden member.

* * * * *